United States Patent
Kim et al.

(10) Patent No.: US 11,417,857 B2
(45) Date of Patent: Aug. 16, 2022

(54) HETEROCYCLIC COMPOUND AND ELECTRONIC APPARATUS

(71) Applicant: Samsung Display Co., Ltd., Yongin-si (KR)

(72) Inventors: Yohan Kim, Yongin-si (KR); Wonmin Yun, Yongin-si (KR); Yisu Kim, Yongin-si (KR); Byoungduk Lee, Yongin-si (KR); Yoonhyeung Cho, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 16/249,775

(22) Filed: Jan. 16, 2019

(65) Prior Publication Data

US 2019/0229290 A1    Jul. 25, 2019

(30) Foreign Application Priority Data

Jan. 24, 2018 (KR) .................. 10-2018-0008951
Jan. 24, 2018 (KR) .................. 10-2018-0008952

(51) Int. Cl.
*H01L 51/52*    (2006.01)
*H01L 51/00*    (2006.01)
(Continued)

(52) U.S. Cl.
CPC ........ *H01L 51/5253* (2013.01); *C07C 233/24* (2013.01); *C07C 233/33* (2013.01); *C07D 211/46* (2013.01); *C07D 249/20* (2013.01); *C07D 401/12* (2013.01); *C08K 5/005* (2013.01); *C09K 3/10* (2013.01); *H01L 51/0067* (2013.01); *H01L 51/0072* (2013.01); *C08K 5/04* (2013.01);
(Continued)

(58) Field of Classification Search
CPC ... H01L 23/29; H01L 51/5253; H01L 31/048; H01L 31/0481; H01L 31/0203; C09K 3/10; C08K 5/005; C08K 5/04; C08K 5/13; C08K 5/16; C08K 5/34
USPC ............................................. 252/75; 428/339
See application file for complete search history.

(56) References Cited

U.S. PATENT DOCUMENTS 4,289,686 A    9/1981    Rody et al.
4,314,933 A    2/1982    Berner
(Continued)

FOREIGN PATENT DOCUMENTS

CN    101367792 B    10/2011
CN    105859607 A    8/2016
(Continued)

OTHER PUBLICATIONS

Cytec Technical Datasheet of Cyasorb (R) UV-531. Sep. 1997 (Year: 1997).*

(Continued)

*Primary Examiner* — Jane L Stanley
(74) *Attorney, Agent, or Firm* — Lewis Roca Rothgerber Christie LLP

(57) ABSTRACT

Provided are a heterocyclic compound and an electronic apparatus. The electronic apparatus includes: a substrate; an organic light-emitting device on the substrate; and a thin film encapsulation portion sealing the organic light-emitting device, the thin film encapsulation portion including an ultraviolet (UV) stabilizing mixture, and the UV stabilizing mixture including a UV absorbent and a radical scavenger.

13 Claims, 4 Drawing Sheets

(51) Int. Cl.
| | |
|---|---|
| *C07D 401/12* | (2006.01) |
| *C07D 211/46* | (2006.01) |
| *C07C 233/24* | (2006.01) |
| *C07C 233/33* | (2006.01) |
| *C07D 249/20* | (2006.01) |
| *C09K 3/10* | (2006.01) |
| *C08K 5/00* | (2006.01) |
| *H01L 27/32* | (2006.01) |
| *C08K 5/13* | (2006.01) |
| *C08K 5/16* | (2006.01) |
| *C08K 5/34* | (2006.01) |
| *C08K 5/04* | (2006.01) |

(52) U.S. Cl.
CPC ............ *C08K 5/13* (2013.01); *C08K 5/16* (2013.01); *C08K 5/34* (2013.01); *H01L 27/3211* (2013.01); *H01L 27/3244* (2013.01)

(56) References Cited

U.S. PATENT DOCUMENTS

| | | | |
|---|---|---|---|
| 5,032,498 | A | 7/1991 | Rody et al. |
| 5,919,933 | A | 7/1999 | Gaa et al. |
| 6,126,861 | A | 10/2000 | Bechtold |
| 6,492,518 | B1 | 12/2002 | Desai et al. |
| 8,941,003 | B2 | 1/2015 | Mandokoro et al. |
| 8,981,011 | B2 | 3/2015 | Chae et al. |
| 9,543,521 | B2 | 1/2017 | Kaihovirta et al. |
| 10,319,944 | B2 | 6/2019 | Lee et al. |
| 2005/0023966 | A1 | 2/2005 | Suh et al. |
| 2005/0043543 | A1 | 2/2005 | Wood et al. |
| 2009/0162307 | A1 | 6/2009 | Fritzsche et al. |
| 2010/0295091 | A1 | 11/2010 | Strzegowski et al. |
| 2011/0303277 | A1 | 12/2011 | Neumann et al. |
| 2013/0102734 | A1 | 4/2013 | Takaragi et al. |
| 2014/0045990 | A1* | 2/2014 | Chae .............. C08F 255/023 524/585 |
| 2016/0017165 | A1 | 1/2016 | Numrich et al. |
| 2016/0329522 | A1* | 11/2016 | Hagihara .......... H01L 51/5253 |

FOREIGN PATENT DOCUMENTS

| | | |
|---|---|---|
| EP | 0 389 427 A2 | 3/1990 |
| EP | 1 405 887 A1 | 4/2004 |
| EP | 2 439 240 A1 | 4/2012 |
| JP | 58-159460 A | 9/1983 |
| JP | 3-139589 A | 6/1991 |
| JP | 11-279150 A | 10/1999 |
| JP | 2989933 B2 | 10/1999 |
| KR | 10-2000-0005350 A | 1/2000 |
| KR | 10-2011-0110357 A | 10/2011 |
| KR | 10-2012-0123222 A | 11/2012 |
| KR | 10-2012-0125617 A | 11/2012 |
| KR | 10-1229678 B1 | 2/2013 |
| KR | 10-2014-0101788 A | 8/2014 |
| KR | 10-2016-0027489 A | 3/2016 |
| KR | 10-2016-0102437 A | 8/2016 |
| WO | WO 97/39051 A1 * | 10/1997 ............ C08K 5/00 |
| WO | WO 2007/087281 A1 | 8/2007 |

OTHER PUBLICATIONS

BASF Technical Datasheet of Tinuvin 770-DF (R). Oct. 2016 (Year: 2016).*
Partial European Search Report for corresponding European Patent Application No. 19153203.5, dated Apr. 15, 2019, 17 pages.
Acosta, Ricardo, et al.; The synthesis and evaluation of novel photosensitisers for controlled degradation of polyethylene, Polymer Degradation and Stability, vol. 52, No. 1, Apr. 1, 1996, Elsevier, pp. 11-17.
Hu, S., et al.; Exploring chromophore tethered aminoethers as potential photoinitiators for controlled radial polymerization, Polymer, Elsevier Science Publishers B.V., GB, vol. 41, No. 2, May 11, 2017, pp. 445-452.
Liu, Naichun, et al.; Synthesis and performance of new bifunctional stabilizers, Polymer Degradation and Stability, Elsevier Science Limited, GB, vol. 62, No. 2, Nov. 1, 1998, pp. 307-314.
Extended European Search Report for corresponding European Patent Application No. 19153203.5, dated Jul. 29, 2019, 20 pages.
Shao, Yuchang, et al.; Synthesis and characterization of light stabilizers of benzotriazole compound containing a hindered amine moiety, Dalian Research and Design Institute of Chemical Industry, Database Caplus [Online] XP-002792705, Chemical Abstracts Service, Columbus Ohio, US, 2007, 24 (12), 2 pages.

* cited by examiner

HETEROCYCLIC COMPOUND AND ELECTRONIC APPARATUS

CROSS-REFERENCE TO RELATED APPLICATIONS

This application claims priority to and the benefit of Korean Patent Application Nos. 10-2018-0008951, filed on Jan. 24, 2018 and 10-2018-0008952, filed on Jan. 24, 2018, in the Korean Intellectual Property Office, the entire content of each of which is incorporated herein by reference.

BACKGROUND

1. Field

One or more embodiments relate to a heterocyclic compound, an electronic apparatus including an organic light-emitting device, and a method of manufacturing the electronic apparatus.

2. Description of the Related Art

An electronic apparatus may include an organic light-emitting device including a hole injection electrode, an electron injection electrode, and an organic emission layer between the hole injection electrode and the electron injection electrode. Organic light-emitting devices are self-emission devices that have wide viewing angles, high contrast ratios, short response times, and excellent characteristics in terms of brightness, driving voltage, and response speed, compared to other devices in the art. For example, an organic light-emitting display apparatus, which is a type (or kind) of electronic apparatus including an organic light-emitting device, is a self-emission apparatus in which holes injected from a hole injection electrode and electrons injected from an electron injection electrode recombine in an organic emission layer to produce excitons. These excitons transit (e.g., transition or relax) from an excited state to a ground state, thereby generating light.

Since an organic light-emitting display apparatus which is a self-emission display apparatus does not require a separate light source, the organic light-emitting display apparatus may be driven at a low voltage, may be configured to be lightweight and thin, and may have excellent characteristics in terms of viewing angles, contrast, and response time. Therefore, applications of such organic light-emitting display apparatuses range from, but are not limited to, personal portable devices such as MP3 players and mobile phones to televisions (TVs).

Additionally, as outdoor use of information devices such as electronic apparatuses including organic light-emitting devices increases, electronic apparatuses including organic light-emitting devices are increasingly being exposed to sunlight. In addition, there are many cases in which an operation involving irradiation of ultraviolet rays is required in a process of manufacturing an organic light-emitting device. Therefore, if the ultraviolet rays are freely transmitted to the inside of the organic light-emitting device, an emission layer or the like including an organic material may be seriously damaged.

SUMMARY

During the manufacturing process of an electronic apparatus such as an organic light-emitting display, when ultraviolet rays or the like are introduced into the apparatus from the outside of the apparatus or penetrate into the apparatus, an emission layer, an insulating film, or the like, including an organic material may be seriously damaged.

Aspects of embodiments of the present disclosure provide an electronic apparatus capable of reducing the amount of ultraviolet rays transmitted into an electronic apparatus. However, these aspects of embodiments are illustrative and the scope of the present disclosure is not limited thereto.

Additional aspects of embodiments will be set forth in part in the description which follows and, in part, will be apparent from the description, or may be learned by practice of the presented embodiments.

An aspect of an embodiment provides an electronic apparatus including:
a substrate;
an organic light-emitting device on the substrate; and
a thin film encapsulation portion sealing the organic light-emitting device,
wherein the thin film encapsulation portion includes an ultraviolet (UV) stabilizing mixture, and
the UV stabilizing mixture includes a UV absorbent and a radical scavenger.

Another aspect of an embodiment provides a heterocyclic compound represented by Formula B1:

$$(A_1)_{m1}\text{-}L_1\text{-}(A_2)_{m2}.$$ <span style="float:right">Formula B1</span>

In Formula B1,
$L_1$ may be an (m1+m2)-valent $C_2$-$C_{20}$ organic group that links $A_1$ and $A_2$,
$A_1$ may be a UV-absorbing group,
$A_2$ may be a radical-scavenging group,
m1 may be an integer from 1 to 3, and
m2 may be an integer from 1 to 3.

Another aspect of an embodiment provides an electronic apparatus including: a substrate; an organic light-emitting device on the substrate; and a thin film encapsulation portion sealing the organic light-emitting device, wherein the thin film encapsulation portion includes the heterocyclic compound.

BRIEF DESCRIPTION OF THE DRAWINGS

These and/or other aspects of embodiments will become apparent and more readily appreciated from the following description of the embodiments, taken in conjunction with the accompanying drawings in which.

DETAILED DESCRIPTION

Figure 1:
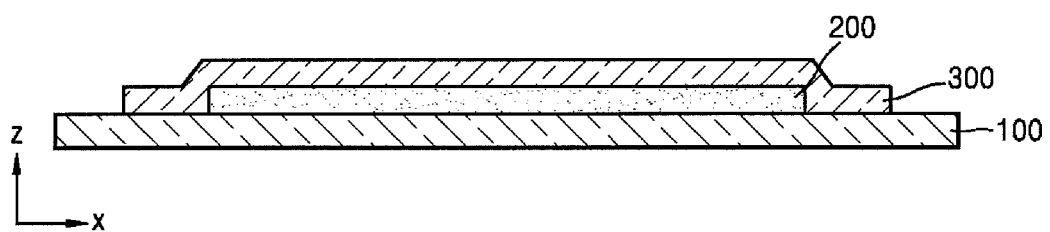
FIGS. 1-2 are schematic cross-sectional views of organic light-emitting display apparatuses as one example of electronic apparatuses, according to an embodiment.

The present disclosure will now be described more fully with reference to exemplary embodiments. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Features of the present disclosure, and how to achieve them, will become apparent by reference to the embodiments that will be described herein in more detail, together with the accompanying drawings. The subject matter of the present disclosure may, however, be embodied in many different forms and should not be limited to the exemplary embodiments.

Hereinafter, embodiments are described in more detail by referring to the attached drawings, and in the drawings, like reference numerals denote like elements, and a redundant explanation thereof will not be provided herein.

It will be understood that when a layer, film, region, or plate is referred to as being "formed on," another layer, film, region, or plate can be directly or indirectly formed on the other layer, film, region, or plate. For example, intervening layers, films, regions, or plates may be present. In addition, sizes of components in the drawings may be exaggerated for convenience of explanation. In other words, since sizes and thicknesses of components in the drawings may be arbitrarily illustrated for convenience of explanation, the following embodiments of the present disclosure are not limited thereto.

Hereinafter, the terms "first," "second," etc. are used only for the purpose of distinguishing one element from another.

In the following embodiments, x-axis, y-axis, and z-axis are not limited to three axes on the orthogonal coordinates system, and may be construed as a broader sense. For example, x-axis, y-axis, and z-axis may be orthogonal to one another, but may indicate different directions that are not orthogonal to one another.

An aspect of an embodiment provides an electronic apparatus including: a substrate; an organic light-emitting device on the substrate; and a thin film encapsulation sealing the organic light-emitting device, wherein the thin film encapsulation includes a UV stabilizing mixture, and the UV stabilizing mixture includes a UV absorbent and a radical scavenger.

For example, the electronic apparatus may include: a substrate; an organic light-emitting device included within a pixel defining region on the substrate; and a thin film encapsulation sealing the organic light-emitting device, wherein the thin film encapsulation includes a UV stabilizing mixture.

Another aspect of an embodiment provides an electronic apparatus including: a substrate; an organic light-emitting device on the substrate; and a thin film encapsulation sealing the organic light-emitting device, wherein the thin film encapsulation includes the heterocyclic compound.

For example, the electronic apparatus may include: a substrate; an organic light-emitting device included in a pixel defining region on the substrate; and a thin film encapsulation sealing the organic light-emitting device, wherein the thin film encapsulation includes the heterocyclic compound. The heterocyclic compound will be described below.

FIG. 1 is a schematic cross-sectional view of an organic light-emitting display apparatus 10 according to an embodiment.

Referring to FIG. 1, the organic light-emitting display apparatus 10 according to an embodiment includes a substrate 100, an organic light-emitting device 200, and a thin film encapsulation 300.

The substrate 100 may be any one of various suitable substrates that are used in an organic light-emitting display apparatus in the related art, and may be an inorganic substrate or an organic substrate, each having high mechanical strength, thermal stability, transparency, surface smoothness, ease of handling, and water repellency.

For example, the substrate 100 may be an inorganic substrate made of a transparent glass material including $SiO_2$ as a main component, but embodiments of the present disclosure are not limited thereto.

In one embodiment, the substrate 100 may be an organic substrate including an insulating organic material. The insulating organic material may be selected from, for example, polyethersulphone (PES), polyacrylate (PAR), polyetherimide (PEI), polyethylene napthalate (PEN), polyethylene terephthalate (PET), polyphenylene sulfide (PPS), polyallylate, polyimide, polycarbonate (PC), cellulose triacetate (TAC), and cellulose acetate propionate (CAP), but embodiments of the present disclosure are not limited thereto.

The organic light-emitting device 200 is disposed on the substrate 100. The organic light-emitting device 200 may include a first electrode, an intermediate layer including an emission layer, and a second electrode.

The first electrode may be formed by, for example, depositing or sputtering a material for a first electrode on the substrate. When the first electrode is an anode, the material for forming the first electrode may be selected from materials having a high work function to facilitate hole injection.

The first electrode may be a reflective electrode. a semi-transmissive electrode, or a transmissive electrode. When the first electrode is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode may have a single-layered structure, or a multi-layered structure including two or more layers. For example, the first electrode may have a three-layered structure of ITO/Ag/ITO, but the structure of the first electrode is not limited thereto.

An interlayer may be disposed on the first electrode, the interlayer including the emission layer.

The interlayer may further include a hole transport region between the first electrode and the emission layer, and an electron transport region between the emission layer and the second electrode, but embodiments of the present disclosure are not limited thereto.

A second electrode may be disposed on the interlayer. The second electrode 190 may be a cathode that is an electron injection electrode, and in this regard, a metal for forming the second electrode may be a material having a low work function, and such a material may be metal, alloy, an electrically conductive compound, or a combination thereof.

The second electrode may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode may be a transmissive electrode, a semi-transmissive electrode, or a reflective electrode.

The first electrode may have a single-layered structure, or a multi-layered structure including two or more layers.

The organic light-emitting device 200 includes a thin film encapsulation 300.

The thin film encapsulation 300 may have a UV stabilizing mixture, and the UV stabilizing mixture may include an UV absorber and a radical scavenger.

In one embodiment, the UV absorber may include at least one UV absorbing compound which is selected from:

a benzophenone-containing compound, a benzoquinone-containing compound, an anthraquinone-containing compound, a xanthone-containing compound, a benzotriazine-containing compound, a benzotriazinone-containing compound, a benzotriazole-containing compound, a benzoate-containing compound, a cyanoacrylate-containing compound, a triazine-containing compound, an oxanilide-containing compound, a salicylate-containing compound, and a pyrene-containing compound, each substituted with a hydroxyl group.

The benzophenone-containing compound may include, for example, 2-hydroxybenzophenone, 2,4-dihydroxybenzophenone, 2-hydroxy-4-methoxybenzophenone, 2-hydroxy-4-octylbenzophenone, 4-dodecyloxy-2-hydroxybenzophenone, 4-benzyloxy-2-hydroxybenzophenone, 2,2',4,4'-tetrahydroxybenzophenone, 2,2'-dihydroxy-4,4'-dimethoxybenzophenone, or the like.

The benzoquinone-containing compound may include, for example 2-hydroxybenzoquinone.

The anthraquinone-containing compound may include, for example, 1-hydroxyanthraquinone, 1,5-hydroxyanthraquinone, 1,8-hydroxyanthraquinone, or the like.

The benzotriazole-containing compound may include, for example, 2-(2-hydroxyphenyl)benzotriazole, 2-(5-methyl-2-hydroxyphenyl)benzotriazole, 2-[2-hydroxy-3,5-bis($\alpha,\alpha$-dimethylbenzyl)phenyl]-2H-benzotriazole, 2-(3,5-di-t-butyl-2-hydroxyphenyl)benzotriazole, 2-(3-t-butyl-5-methyl-2-hydroxyphenyl)-5-chlorobenzotriazole, 2-(3,5-di-t-butyl-2-hydroxyphenyl)-5-chlorobenzotriazole, 2-(3,5-di-t-acyl-2-hydroxyphenyl)benzotriazole, 2-(2'-hydroxy-5'-t-octylphenyl)benzotriazole, or the like.

The benzoate-containing compound may include, for example, phenyl 2-hydroxybenzoate, 2,4-di-t-butylphenyl-3',5'-di-t-butyl-4-hydroxybenzoate, or the like.

The triazine-containing compound may include, for example 2-(4,6-diphenyl-1,3,5-triazine-2-yl)phenol, 2-(4,6-diphenyl-1,3,5-triazine-2-yl)-5-(hexyl)oxy-phenol, 2-[4-[(2-hydroxy-3-dodecyloxypropyl)oxy]-2-hydroxyphenyl]-4,6-bis(2,4-dimethylphenyl)-1,3,5-triazine, or the like.

The salicylate-containing compound may include, for example, phenylsalicylate, 4-t-butylphenylsalicylate, or the like.

In one embodiment, the UV absorbing compound may be represented by one selected from Formulae A1-1 to A1-3:

Formula A1-1

Formula A1-2

Formula A1-3

In Formulae A1-1 to A1-3, $CY_1$ and $CY_2$ may each independently be selected from a benzene group, a naphthalene group, an anthracene group, a pyrene group, and a phenanthrene group, $R_1$ and $R_2$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, $R_1$ and $R_2$ may optionally be linked to form a —$(Y_1)_{k1}$— linking group, $Y_1$ may be —O—, —S—, or —C(=O)—, k1 may be an integer from 1 to 3, one of $Y_2$ and $Y_3$ may be N, and the other may be a single bond, a double bond, or —C(=O)—, $R_{10}$, $R_{20}$, $R_{30}$, and $R_{40}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$, a10 may be an integer from 1 to 18, a20 may be an integer from 1 to 4, a30 may be an integer from 1 to 5, a40 may be an integer from 1 to 4, at least one of $R_{10}$(s) in the number of a10 may be a hydroxyl group, at least one of $R_{20}$(s) in the number of a20 may be a hydroxyl group, at least one of $R_{30}$(s) in the number of a30 may be a hydroxyl group, at least substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $—Si(Q_{11})(Q_{12})(Q_{13})$, $—N(Q_{11})(Q_{12})$, $—B(Q_{11})(Q_{12})$, $—C(=O)(Q_{11})$, $—S(=O)_2(Q_{11})$, and $—P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $—Si(Q_{21})(Q_{22})(Q_{23})$, $—N(Q_{21})(Q_{22})$, $—B(Q_{21})(Q_{22})$, $—C(=O)(Q_{21})$, $—S(=O)_2(Q_{21})$ and $—P(=O)(Q_{21})(Q_{22})$; and $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

In one embodiment, in Formulae A1-1 to A1-3, $R_1$ and $R_2$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, wherein $R_1$ and $R_2$ may optionally be linked to form a $—(Y_1)_{k1}—$ linking group, wherein $—(Y_1)_{k1}—$ may be $—O—$, $—S—$, $—$ or $—C(=O)—$.

For example, $R_1$ and $R_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group, wherein $R_1$ and $R_2$ may be linked to form a $—(Y_1)_{k1}—$ linking group, wherein $—(Y_1)_{k1}—$ may be $—O—$, $—S—$, or $—C(=O)—$.

In one embodiment, in Formulae A1-1 to A1-3, $R_{10}$, $R_{20}$, $R_{30}$, and $R_{40}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{00}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

For example, $R_{10}$, $R_{20}$, $R_{30}$, and $R_{40}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

In one embodiment, the UV absorbing compound may be represented by one selected from Formulae A2-1 to A2-9:

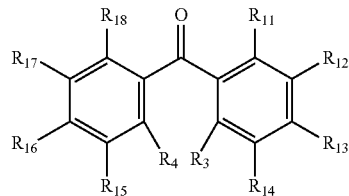

A2-1

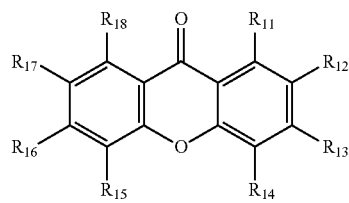

A2-2

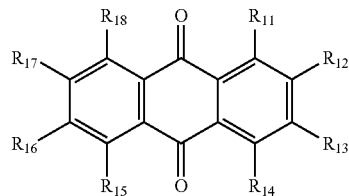

A2-3

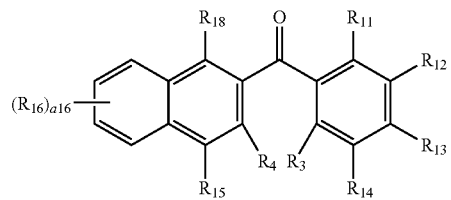

A2-4

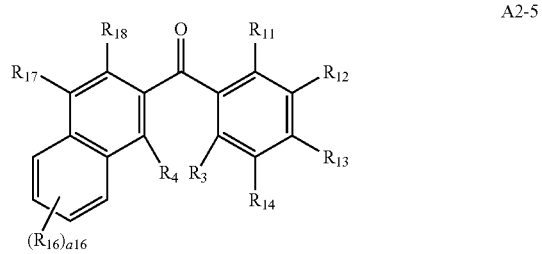

A2-5

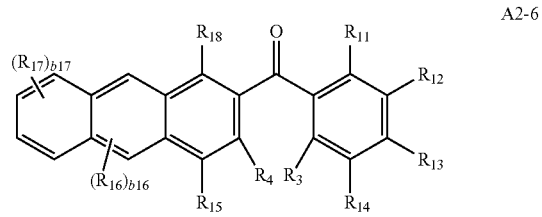

A2-6

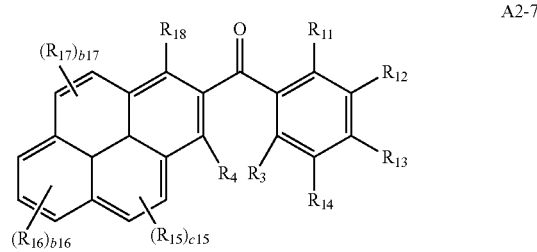

A2-7

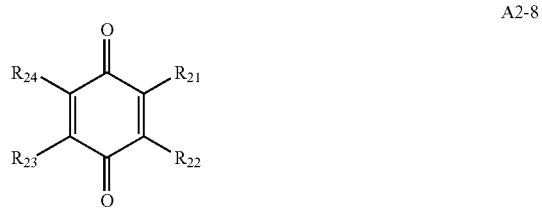

A2-8

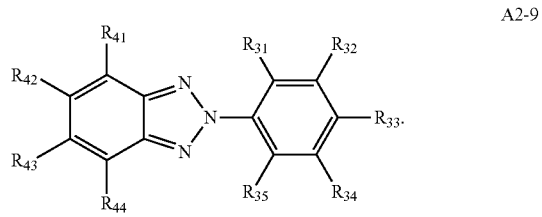

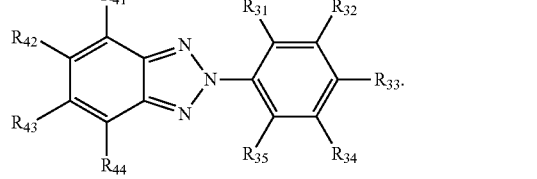

A2-9

In Formulae A2-1 to A2-9, $R_3$, $R_4$, and $R_{11}$ to $R_{18}$ are the same as described in connection with $R_{10}$, a16 may be 1, 2, 3, or 4, b16 may be 1 or 2, b17 may be 1, 2, 3, or 4, c15 may be 1 or 2, c16 may be 1, 2, or 3, c17 may be 1 or 2, $R_{21}$ to $R_{24}$ are the same as described in connection with $R_{20}$, $R_{31}$ to $R_{35}$ are the same as described in connection with $R_{30}$, $R_{41}$ to $R_{44}$ are the same as described in connection with $R_{40}$, and at least one of $R_{11}$ to $R_{18}$, at least one of $R_{21}$ to $R_{24}$, and at least one of $R_{31}$ to $R_{35}$ may be a hydroxyl group.

In one embodiment, at least one of $R_{11}$, $R_{15}$, and $R_{18}$ in Formulae A2-1 to A2-7 may be a hydroxyl group. For example, at least one of $R_{11}$ and $R_{18}$ may be a hydroxyl group, but embodiments of the present disclosure are not limited thereto.

In one embodiment, $R_{21}$ in Formula A2-8 may be a hydroxyl group.

In one embodiment, at least one of $R_{31}$ and $R_{35}$ in Formula A2-9 may be a hydroxyl group.

In one embodiment, the UV-absorbing compound may be represented by one selected from Formulae A3-1 to A3-9:

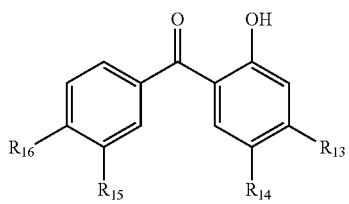
A3-1

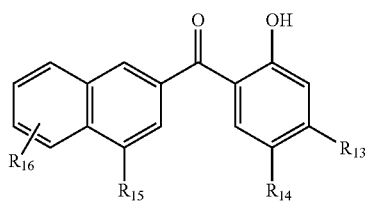
A3-2

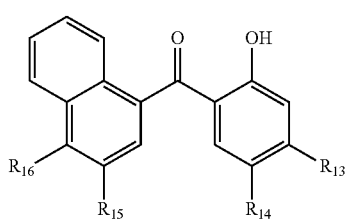
A3-3

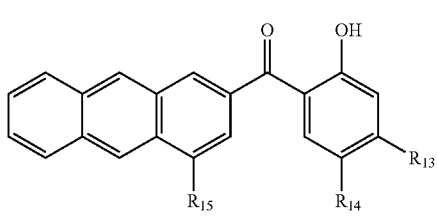
A3-4

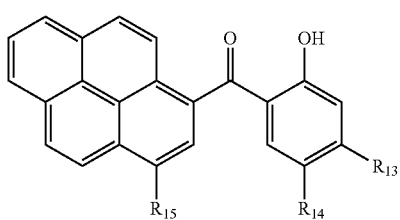
A3-5

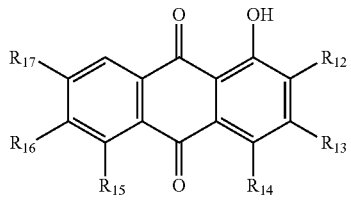
A3-6

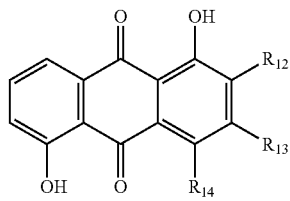
A3-7

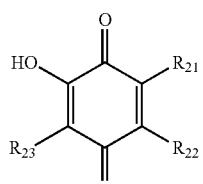
A3-8

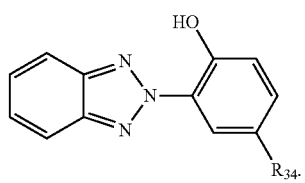
A3-9

In Formulae A3-1 to A3-9, $R_{13}$ to $R_{17}$ are the same as described in connection with $R_{10}$, $R_{21}$ to $R_{23}$ are the same as described in connection with $R_{20}$, and $R_{34}$ is the same as described in connection with $R_{30}$.

In one embodiment, the UV absorbent may include a first UV-absorbing compound and a second UV-absorbing compound, The first UV-absorbing compound and the second UV-absorbing compound may each independently be selected from a benzophenone-containing compound, a benzoquinone-containing compound, an anthraquinone-containing compound, a xanthone-containing compound, a benzotriazine-containing compound, a benzotriazinone-containing compound, a benzotriazole-containing compound, a benzoate-containing compound, a cyanoacrylate-containing compound, a triazine-containing compound, an oxanilide-containing compound, a salicylate-containing compound, and a pyrene-containing compound, each substituted with a hydroxyl group, and a wavelength range of light absorbed by the first UV-absorbing compound may be different from a wavelength range of light absorbed by the second UV-absorbing compound.

The UV absorbent may absorb ultraviolet rays and prevent the ultraviolet rays from penetrating the organic light-emitting device 200 (or reduce the amount of ultraviolet rays that penetrate the organic light-emitting device 200). Therefore, the organic light-emitting display apparatus 10 including the UV absorbent in the thin film encapsulation 300 may prevent the emission layer, the insulating film, or the like, including the organic material, from being damaged by the ultraviolet rays (or may reduce a likelihood or degree of such damage).

In one embodiment, the UV absorbent may absorb a wavelength of about 280 nm to about 430 nm.

In one embodiment, the radical scavenger may include at least one of the radical-scavenging compound, and the radical-scavenging compound may be selected from a phenol-containing compound, a hindered amine-containing compound, and a phenylenediamine-containing compound.

In one embodiment, the radical scavenger may include at least one compound represented by one selected from Formulae A4-1 to 4-3:

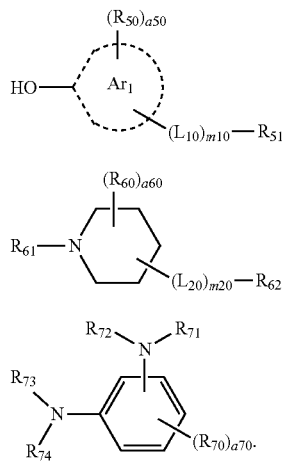

Formula A4-1

Formula A4-2

Formula A4-3

In Formulae A4-1 to A4-3, ring $Ar_1$ may be a benzene ring or a naphthalene ring, $L_{10}$ and $L_{20}$ may each independently be —O—, —S—, $S(=O)_2$—, —C(=O)—, —C(=O)O—, —C(=O)NH—, a $C_1$-$C_{30}$ hydrocarbon group, a $C_5$-$C_{60}$ carbocyclic group, or a $C_2$-$C_{30}$ heterocyclic group, m10 and m20 may each independently be an integer from 0 to 5, wherein, when m10 is two or more, two or more $L_{10}$(s) may be identical to or different from each other, and when m10 is 0, $L_{10}$ may be a single bond, and when m20 is two or more, two or more $L_{20}$(s) may be identical to or different from each other, and when m20 is 0, $L_{20}$ may be a single bond, $R_{50}$, $R_{51}$, $R_{60}$, $R_{61}$, $R_{62}$, and $R_{70}$ to $R_{74}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, a50 may be an integer from 1 to 6, a60 may be an integer from 1 to 4, a70 may be an integer from 1 to 4, when a50 is two or more, two or more $R_{50}$(s) may be identical to or different from each other, when a60 is two or more, two or more $R_{60}$(s) may be identical to or different from each other, when a70 is two or more, two or more $R_{70}$(s) may be identical to or different from each other, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{00}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$) and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

In one embodiment, in Formulae A4-1 to A4-3,
$L_{10}$ and $L_{20}$ may each independently be selected from:
—O—, —S—, S(=O)$_2$—, —C(=O)—, —C(=O)O—, and —C(=O)NH—;

a $C_1$-$C_{20}$ alkylene group, a $C_2$-$C_{20}$ alkenylene group, a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group; and a $C_1$-$C_{20}$ alkylene group, a $C_2$-$C_{20}$ alkenylene group, a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

In one or more embodiments, in Formulae A4-1 to A4-3, one of $L_{10}$ and $L_{20}$ may be selected from:
a $C_6$-$C_{30}$ alkylene group, a $C_6$-$C_{30}$ alkenylene group, and a $C_6$-$C_{30}$ alkynylene group; and a $C_6$-$C_{30}$ alkylene group, a $C_6$-$C_{30}$ alkenylene group, and a $C_6$-$C_{30}$ alkynylene group, each substituted with at least one substituent selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si($Q_{31}$)($Q_{32}$)($Q_{33}$), or one of $R_{50}$, $R_{51}$, $R_{60}$, $R_{61}$, and $R_{70}$ to $R_{74}$ may be selected from:

a $C_6$-$C_{30}$ alkyl group, a $C_6$-$C_{30}$ alkoxy group, a $C_6$-$C_{30}$ alkenyl group, and a $C_6$-$C_{30}$ alkynyl group; and a $C_6$-$C_{30}$ alkyl group, a $C_6$-$C_{30}$ alkoxy group, a $C_6$-$C_{30}$ alkenyl group, and a $C_6$-$C_{30}$ alkynyl group, each substituted with at least one substituent selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si($Q_{31}$)($Q_{32}$)($Q_{33}$).

In one embodiment, at least one selected from $L_{10}$, $L_{20}$, $R_{50}$, $R_{51}$, $R_{60}$, $R_{61}$, and $R_{70}$ to $R_{74}$ may include a hydrocarbon chain consisting of six or more carbon atoms, thereby improving miscibility with other constituents in the thin film encapsulation.

In one embodiment, the radical scavenger may include at least one compound represented by one selected from Formulae A5-1 to A5-4:

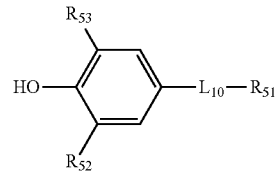

A5-1

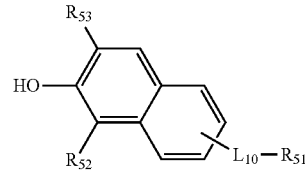

A5-2

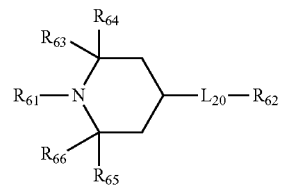

A5-3

-continued

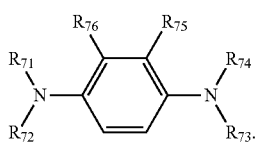

A5-4

In Formulae A5-1 to A5-4, $R_{51}$ to $R_{53}$, $R_{61}$ to $R_{66}$, and $R_{71}$ to $R_{76}$ may each independently be selected from:

deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, and $L_{10}$ and $L_{20}$ are each independently the same as described above.

The phenol-containing compound may be butylated hydroxyanisole (BHA), butylated hydroxytoluene (BHT), tert-butylhydroquinone (TBHQ), propyl gallate (PG), catecol(1,2-benzenediol), 1,2-naphthalenediol, or the like.

The hindered amine-containing compound may be bis-(2,2,6,6-tetramethyl-4-piperidyl)sebacate, bis-(N-methyl-2,2,6,6-tetramethyl-4-piperidyl)sebacate, bis-(1,2,2,6,6-pentamethyl-4-piperidyl)sebacate, 1,2,2,6,6-pentamethyl-4-piperidyl-tridecyl-1,2,3,4-butanetetracarboxylate, tetrakis-(2,2,6,6-tetramethyl-4-piperidyl)-1,2,3,4-butanetetracarboxylate, tetrakis-(N-methyl-2,2,6,6-tetramethyl-4-piperidyl)-1,2,3,4-butanetetracarboxylate, or the like.

The phenylenediamine-containing compound may be o-phenylenediamine, m-phenylenediamine, p-phenylenediamine, or the like; or o-phenylenediamine, m-phenylenediamine, or p-phenylenediamine, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, and a $C_1$-$C_{20}$ alkoxy group.

In one embodiment, the amount of the radical scavenger may be in a range of about 0.5 parts by weight to about 20 parts by weight based on 100 parts by weight of the UV absorbent. When the amount of the radical scavenger is within this range, the optical stability of the thin film encapsulation due to the radical scavenger is high so that the thin film encapsulation effectively protects the organic light-emitting device from ultraviolet rays. When the amount of the radical scavenger is less than about 0.5 parts by weight, the optical stability of the thin film encapsulation may not be sufficiently secured, and when the amount of the radical scavenger exceeds 20 parts by weight, the transmittance of the thin film encapsulation in a visible ray region may be hindered, and the luminescent efficiency of the organic light-emitting device (for example, a blue organic light-emitting device having a maximum emission wavelength of about 430 nm to about 460 nm) may be hindered.

In one embodiment, the thin film encapsulation 300 may further include a matrix resin, and the UV absorbent may be dispersed in the matrix resin. At this time, the UV absorbent may be simply dispersed in the matrix resin. Alternatively, the UV absorbent may be cross-linked to the matrix resin. For example, the UV absorbent may include the polymeric functional group, and the UV absorbent may be cross-linked to the matrix resin.

In one embodiment, the thin film encapsulation 300 may further include a photopolymerization initiator. The photopolymerization initiator may use any suitable one available in the art without any special limitation, and may use those that are curable at a wavelength of, for example, about 360 nm to about 420 nm.

In one embodiment, the thin film encapsulation 300 may further include at least two types (or kinds) of the photopolymerization initiator. For example, one of the at least two types (or kinds) of the photopolymerization initiator may be curable in a UV region (at a wavelength of, for example, about 360 nm to about 420 nm), and the other may be curable in a visible ray region (for example, at a wavelength of, for example, about 400 nm to about 770 nm). In one or more embodiments, the at least two types (or kinds) of the photopolymerization initiator may be all curable in a UV region or a visible ray region.

In one embodiment, the thin film encapsulation 300 may further include at least one selected from a metal, a metal halide, a metal nitride, a metal oxide, a metal oxynitride, a silicon nitride, a silicon oxide, and a silicon oxynitride.

For example, the thin film encapsulation 300 may include at least one selected from $MgF_2$, LiF, $AlF_3$, NaF, a silicon oxide, a silicon nitride, a silicon oxynitride, an aluminum oxide, an aluminum nitride, an aluminum oxynitride, a titanium oxide, a titanium nitride, a tantalum oxide, a tantalum nitride, a hafnium oxide, a hafnium nitride, a zirconium oxide, a zirconium nitride, a cerium oxide, a cerium nitride, a tin oxide, a tin nitride, and a magnesium oxide, but embodiments of the present disclosure are not limited thereto.

In one embodiment, the thin film encapsulation 300 may include at least one organic film. The at least one organic film may include a first organic film, and the UV stabilizing mixture may be included in the first organic film.

In one embodiment, the thin film encapsulation (for example, the first organic film) including the UV stabilizing mixture may have a transmittance of about 10% or less (for example, 8%) with respect to light having a wavelength of about 400 nm to about 410 nm (for example, 405 nm).

In one or more embodiments, the thin film encapsulation (for example, the first organic film) including the UV stabilizing mixture may have a transmittance of about 80% (for example, 90% or more) with respect to light having a wavelength of about 430 nm or more, and may have a transmittance of about 10% or less with respect to light having a wavelength of about 405 nm or less.

In one embodiment, when the first organic film is exposed to an exposure amount of 52,000 $Wh/m^2$, a change in transmittance with respect to a wavelength range of about 400 nm to about 410 nm is may be less than 5%.

In one or more embodiments, when the first organic film is exposed to an exposure amount of about 52,000 Wh/m², a change in transmittance with respect to a wavelength range of about 400 nm to about 405 nm may be less than 3%.

In one or more embodiments, when the first organic film is exposed to light having a maximum emission wavelength of about 405 nm or light having a wavelength range of about 380 nm to about 410 nm with respect to an exposure amount of about 52,000 Wh/m², a change in transmittance with respect to a wavelength range of about 400 nm to about 410 nm may be less than 5%.

In one or more embodiments, when the first organic film is exposed to light having a maximum emission wavelength of about 405 nm or light having a wavelength range of about 380 nm to about 410 nm in an exposure amount of about 52,000 Wh/m², a change in transmittance with respect to a wavelength range of about 400 nm to 405 nm may be less than 3%.

The change in transmittance in the above wavelength range may be measured by, for example, exposing the first organic film by using an LED lamp emitting light having a wavelength range of about 380 nm to about 410 nm and a maximum emission wavelength of about 405 nm.

In one embodiment, a thickness of the first organic film may be in a range of about 10 nm to about 20 μm, for example, about 10 nm to about 10 μm.

In one embodiment, the amount of the UV stabilizing mixture may be in a range of about 3 parts by weight to about 10 parts by weight based on 100 parts by weight of the first organic film. By controlling the amount of the UV stabilizing mixture in the first organic film, a maximum absorption wavelength of the first organic film may be finely adjusted, and a UV absorption spectrum may be controlled.

For example, the at least one organic film may consist of the UV stabilizing mixture.

In one embodiment, the at least one organic film may further include, in addition to the UV stabilizing mixture, the matrix resin, and the UV stabilizing mixture may be dispersed in the matrix resin. At this time, the UV stabilizing mixture may be simply dispersed in the matrix resin, or the UV stabilizing mixture may be cross-linked to the matrix resin.

In one embodiment, the first organic film may further include a matrix resin, and the matrix resin may include at least one selected from an acryl-based resin, a methacryl-based resin, an isoprene-based resin, a vinyl-based resin, an epoxy-based resin, a urethane-based resin, a cellulose resin, a perylene-based resin, an imide-based resin, and a silicone-based resin.

In one embodiment, the at least one organic film may further include, in addition to the UV stabilizing mixture, a photopolymerization initiator. The photopolymerization initiator is the same as described above.

In one embodiment, the at least one organic film may further include, in addition to the UV stabilizing mixture, the matrix resin and the photopolymerization initiator.

The at least one organic film may be formed in a set or predetermined region by using various suitable methods, such as vacuum deposition, spin-coating, casting, Langmuir-Blodgett (LB), inkjet printing, laser printing, or laser induced thermal imaging (LITI). The number and thickness of organic films may be appropriately selected by taking into account productivity or device characteristics.

In one embodiment, the thin film encapsulation may further include at least one inorganic film, and the at least one inorganic film may further include a first inorganic film.

In one embodiment, the inorganic film may include at least one selected from a metal, a metal halide, a metal nitride, a metal oxide, a metal oxynitride, a silicon nitride, a silicon oxide, and a silicon oxynitride.

For example, the inorganic film may include at least one selected from $MgF_2$, LiF, $AlF_3$, NaF, a silicon oxide, a silicon nitride, a silicon oxynitride, an aluminum oxide, an aluminum nitride, an aluminum oxynitride, a titanium oxide, a titanium nitride, a tantalum oxide, a tantalum nitride, a hafnium oxide, a hafnium nitride, a zirconium oxide, a zirconium nitride, a cerium oxide, a cerium nitride, a tin oxide, a tin nitride, and a magnesium oxide, but embodiments of the present disclosure are not limited thereto.

The at least one inorganic film may be formed in a set or predetermined region by using various suitable methods, such as chemical vapor deposition (CVD), plasma-enhanced chemical vapor deposition (PECVD), sputtering, atomic layer deposition (ALD), or thermal evaporation. The number and thickness of inorganic films may be appropriately selected by taking into account productivity or device characteristics.

In one embodiment, the at least one organic film may include a first organic film, the at least one inorganic film may include a first inorganic film, the first organic film may be disposed between the organic light-emitting device 200 and the first inorganic film. For example, the at least one organic film may include a first organic film, the at least one inorganic film may include a first inorganic film, and the first organic film and the second inorganic film may be sequentially stacked from the organic light-emitting device 200 in this stated order. It should be understood that the term "sequentially stacked" does not exclude that another film is disposed between the organic light-emitting device 200 and the first organic film, and/or between the first organic film and the first inorganic film.

In one or more embodiments, the at least one organic film may include a first organic film, the at least one inorganic film may include a first inorganic film, and the first inorganic film may be disposed between the organic light-emitting device 200 and the first organic film. For example, the at least one organic film may include a first organic film, the at least one inorganic film may include a first inorganic film, and the first inorganic film and the first organic film may be sequentially stacked from the organic light-emitting device 200 in this stated order.

In one or more embodiments, the at least one organic film may include a first organic film, the at least one inorganic film may include a first inorganic film and a second inorganic film, and the first inorganic film, the first organic film, and the second inorganic film may be sequentially stacked from the organic light-emitting device 200 in this stated order.

In one or more embodiments, the at least one organic film may include a first organic film and a second organic film, the at least one inorganic film may include a first inorganic film, and the first organic film, the first inorganic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first inorganic film, the first organic film, and the second inorganic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first organic film, the first inorganic film, the second organic film, and the second inorganic film may be sequentially stacked from the organic light-emitting device 200 in this stated order.

In one or more embodiments, the at least one organic film may include a first organic film and a second organic film, the at least one inorganic film may include a first inorganic film and a second inorganic film, the first inorganic film, the second inorganic film, the first organic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first organic film, the second organic film, the first inorganic film, and the second inorganic film may be sequentially stacked from the organic light-emitting device 200 from this stated order.

In one or more embodiments, the at least one organic film may include a first organic film and a second organic film, the at least one inorganic film may include a first inorganic film, a second inorganic film, and a third inorganic film, the first inorganic film, the first organic film, the second inorganic film, the second organic film, and the third inorganic film may be sequentially stacked from the organic light-emitting device 200 from this stated order.

In one or more embodiments, the at least one organic film may include a first organic film, a second organic film, and a third organic film, the at least one inorganic film may include a first inorganic film and a second inorganic film, the first organic film, the first inorganic film, the second organic film, the second inorganic film, and the third organic film may be sequentially stacked from the organic light-emitting device 200 in this stated order, but embodiments of the present disclosure are not limited thereto. The number of organic films and inorganic films, and the stacking order of the inorganic films and the organic films may be appropriately modified according to the design.

The organic light-emitting display apparatus 10 may include a plurality of organic light-emitting devices 200. In one embodiment, the organic light-emitting display apparatus 10 may include: a substrate, an organic emission unit including a plurality of organic light-emitting devices 200 on the substrate; and a thin film encapsulation 300 sealing the organic emission unit, wherein the thin film encapsulation 300 includes a UV stabilizing mixture. The UV stabilizing mixture is the same as described above.

For example, the thin film encapsulation 300 may include the UV stabilizing mixture and may further include, in addition to the UV stabilizing mixture, a matrix resin. The matrix resin is the same as described above.

In one embodiment, the thin film encapsulation 300 may further include, in addition to the UV stabilizing mixture, a metal, a metal halide, a metal nitride, a metal oxide, a metal oxynitride, a silicon nitride, a silicon oxide, and a silicon oxynitride.

In one embodiment, the thin film encapsulation 300 may include at least one organic film and at least one inorganic film, and the at least one organic film may include the UV absorbent. The at least one organic film and the at least one inorganic film are the same as described above.

Another aspect of an embodiment provides a method of manufacturing an electronic apparatus, including:
forming an organic light-emitting device on a substrate; and
forming a thin film encapsulation sealing the organic light-emitting device on the substrate,
wherein the forming of the thin film encapsulation includes providing a thin film encapsulation composition sealing the organic light-emitting device and curing the thin film encapsulation composition,
the thin film encapsulation composition includes a UV stabilizing mixture, and
the UV stabilizing mixture includes a UV absorbent and a radical scavenger.

The thin film encapsulation, the UV stabilizing mixture, the UV absorbent, and the radical scavenger are the same as described above. When the electronic apparatus is manufactured according to the above-described method, external UV rays are blocked from reaching the organic light-emitting device, thereby preventing a damage from occurring when the organic light-emitting device is continuously exposed to the UV rays (or reducing a likelihood or degree of such damage), and improving the durability of the organic light-emitting device and the electronic apparatus including the same.

In one embodiment, the thin film encapsulation composition may further include a matrix resin monomer and a photopolymerization initiator.

The matrix resin monomer may form a matrix resin included in the thin film encapsulation by photopolymerization. For example, the matrix resin monomer may undergo a photopolymerization reaction by the photopolymerization initiator to form the matrix resin included in the thin film encapsulation. The photopolymerization initiator is the same as described above.

Figure 2:
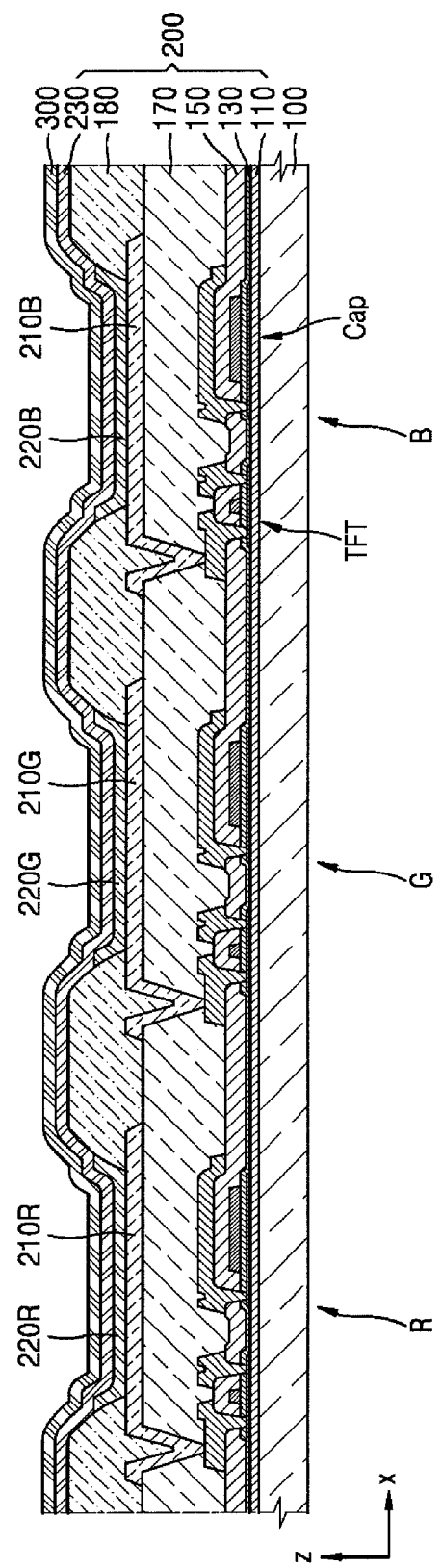

FIG. 2 is a schematic cross-sectional view of an organic light-emitting display apparatus as one of electronic apparatuses according to an embodiment.

Referring to FIG. 2, a backplane is formed. The backplane may be understood as including at least a substrate 100, a plurality of first electrodes 210R, 210G, and 210B on the substrate 100, and a pixel defining film 180 formed to expose at least a portion including the central portions of the first electrodes 210R, 210G, and 210B. The pixel defining film 180 may have a shape protruding from the first electrodes 210R, 210G, and 210B in a +z direction with respect to the substrate 100.

The first electrodes 210R, 210G, and 210B may be understood as pixel electrodes. A pixel electrode 210B, a pixel electrode 210R, and a pixel electrode 210G among the pixel electrodes may be understood as a first pixel electrode, a second electrode, and a third electrode, respectively. This is because intermediate layers formed on the first to third pixel electrodes may be different. For convenience, the terms "pixel electrode 210R", "pixel electrode 210G", and "pixel electrode 210B" are used instead of the first pixel electrode, the second pixel electrode, and the third pixel electrode. The pixel electrodes are the same as described in connection with the first electrode.

The pixel defining film 180 may have an opening corresponding to each subpixel, that is, an opening exposing the central portions of the pixel electrodes 210R, 210G, and 210B or the entire pixel electrodes 210R, 210G, and 210B, thereby defining pixels. In addition, the pixel defining film 180 may increase a distance between the ends of the pixel electrodes 210R, 210G, and 210B and the second electrode (not illustrated) on the pixel electrodes 210R, 210G, and 210B, thereby preventing arc or the like from being generated at the ends of the pixel electrodes 210R, 210G, and 210B (or reducing a likelihood or degree of such arcing).

The backplane may further include, if necessary, other various suitable components. For example, as illustrated in FIG. 2, a thin film transistor TFT or a capacitor Cap may be formed on the 100. The backplane may include components, such as a buffer layer 110 for preventing impurities from penetrating (or reducing a likelihood or amount of the impurities penetrating) a semiconductor layer of the thin film transistor TFT, a gate insulating film 130 for insulating the semiconductor layer of the thin film transistor TFT from the gate electrode, an interlayer insulating film 150 for insulating a source electrode/drain electrode of the thin film transistor TFT and a gate electrode, and a planarization film 170 covering the thin film transistor TFT and having an approximately flat upper surface.

After the backplane is formed, intermediate layers 220R, 220G, and 220B are formed. The intermediate layers 220R, 220G, and 220B may have a multi-layered structure including an emission layer. In this case, unlike those illustrated, some of the intermediate layers 220R, 220G, and 220B may be a common layer approximately corresponding to the entire surface of the substrate 100, and some of the intermediate layers 220R, 220G, and 220B may be a pattern layer patterned corresponding to the pixel electrodes 210R, 210G, and 210B.

After the intermediate layers 220R, 220G, and 220B, a second electrode 230 is formed on the intermediate layers 220R, 220G, and 220B.

After the second electrode 230 is formed, a thin film encapsulation 300 is formed so as to protect the organic light-emitting devices 200 including the pixel electrodes 210R, 210G, and 210B, the intermediate layers 220R, 220G, and 220B, and the second electrode 230 from impurities such as external oxygen or moisture.

The thin film encapsulation 300 may extend to cover not only the upper surface but also the side surfaces of the organic light-emitting device 200 and contact part of the substrate 100. Therefore, it is possible to effectively prevent external oxygen and moisture from penetrating the organic light-emitting device 200 (or to reduce a likelihood or amount of the external oxygen and moisture that penetrates the organic light-emitting device 200).

The thin film encapsulation 300 includes the UV stabilizing mixture.

[Heterocyclic Compound]

Another aspect of an embodiment provides a heterocyclic compound represented by Formula B1.

The heterocyclic compound is represented by Formula B1:

$(A_1)_{m1}\text{-}L_1\text{-}(A_2)_{m2}.$     Formula B1

$L_1$ in Formula B1 is an (m1+m2)-valent $C_2$-$C_{20}$ organic group that links $A_1$ and $A_2$.
In one embodiment, $L_1$ may be a group represented by Formula B2:

$\text{*-}(X_1)_{n1}\text{-}L_{11}\text{-}(X_2)_{n2}\text{-*'}.$     Formula B2

In Formula B1, $X_1$ and $X_2$ may each independently be a single bond, —O—, —S—, —C(=O)—, —C(=O)O—, *—CONH—, or —NHC(=O)NH—, $L_{11}$ may be selected from:
a $C_2$-$C_{12}$ alkylene group, a $C_2$-$C_{12}$ alkenylene group, and a $C_2$-$C_{12}$ alkynylene group; and
a $C_2$-$C_{12}$ alkylene group, a $C_2$-$C_{12}$ alkenylene group, and a $C_2$-$C_{12}$ alkynylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, $N(Q_{31})(Q_{32})$, and —$Si(Q_{31})(Q_{32})(Q_{33})$, n1 and n2 may each independently be an integer from 1 to 3, $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

—NHC(=O)NH— has the following structure:

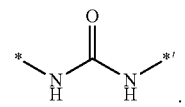

In the above structure, * and *' each indicate a binding site to a neighboring atom.

In one embodiment, $L_1$ may be a group represented by one selected from Formulae B2-1 to B2-5:

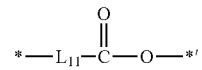     Formula B2-1

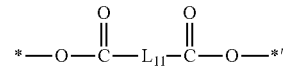     Formula B2-2

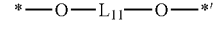     Formula B2-3

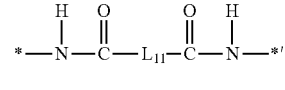     Formula B2-4

     Formula B2-5

In Formulae B2-1 to B2-5,
$L_{11}$ is the same as described herein, and
* and *' each indicate a binding site to a neighboring atom.

In one embodiment, $L_{11}$ may be an ethylene group, a propylene group, a butylene group, a pentylene group, a hexylene group, a heptylene group, an octylene group, a nonylene group, a decanylene group, an undecylene group, and a dodecylene group; and an ethylene group, a propylene group, a butylene group, a pentylene group, a hexylene group, a heptylene group, an octylene group, a nonylene group, a decanylene group, an undecylene group, and a dodecylene group, each substituted with at least one substituent selected from deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group.

In Formula B1, $A_1$ may be a UV-absorbing group.

In one embodiment, $A_1$ may include at least one group selected from a hydroxy benzophenone-containing group, a benzoquinone-containing group, an anthraquinone-containing group, a xanthone-containing group, a benzotriazine-containing group, a benzotriazinone-containing group, a benzotriazole-containing group, a benzoate-containing group, a cyanoacrylate-containing group, a triazine-containing group, an oxanilide-containing group, a salicylate-containing group, and a pyrene-containing group.

The benzophenone-continuing group may include, for example, 2-hydroxybenzophenone, 2,4-dihydroxybenzophenone, 2-hydroxy-4-methoxybenzophenone, 2-hydroxy-4-octylbenzophenone, 4-dodecyloxy-2-hydroxybenzophenone, 4-benzyloxy-2-hydroxybenzophenone, 2,2',4,4'-tetrahydroxybenzophenone, 2,2'-dihydroxy-4,4'-dimethoxybenzophenone, or the like.

The benzoquinone-containing group may include, for example, 2-hydroxybenzoquinone.

The anthraquinone-containing group may include, for example, 1-hydroxyanthraquinone, 1,5-hydroxyanthraquinone, 1,8-hydroxyanthraquinone, or the like.

The benzotriazole-containing group may include, for example, 2-(2-hydroxyphenyl)benzotriazole, 2-(5-methyl-2-hydroxyphenyl)benzotriazole, 2-[2-hydroxy-3,5-bis(α,α-dimethylbenzyl)phenyl]-2H-benzotriazole, 2-(3,5-di-t-butyl-2-hydroxyphenyl)benzotriazole, 2-(3-t-butyl-5-methyl-2-hydroxyphenyl)-5-chlorobenzotriazole, 2-(3,5-di-t-butyl-2-hydroxyphenyl)-5-chlorobenzotriazole, 2-(3,5-di-t-acyl-2-hydroxyphenyl)benzotriazole, 2-(2'-hydroxy-5'-t-octylphenyl)benzotriazole, or the like.

The benzoate-containing group may include, for example, phenyl 2-hydroxybenzoate, 2,4-di-t-butylphenyl-3',5'-di-t-butyl-4-hydroxybenzoate, or the like.

The triazine-containing group may include, for example, 2-(4,6-diphenyl-1,3,5-triazine-2-yl)phenol, 2-(4,6-diphenyl-1,3,5-triazine-2-yl)-5-(hexyl)oxy-phenol, 2-[4-[(2-hydroxy-3-dodecyloxypropyl)oxy]-2-hydroxyphenyl]-4,6-bis(2,4-dimethylphenyl)-1,3,5-triazine.

The salicylate-containing group may include, for example, phenyl salicylate, 4-t-butylphenyl salicylate, or the like.

In an embodiment, $A_1$ may be a group represented by one selected from Formulae B3-1 to B3-3:

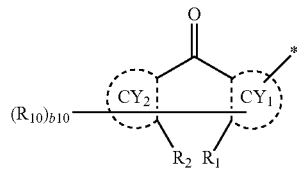

Formula B3-1

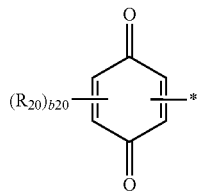

Formula B3-2

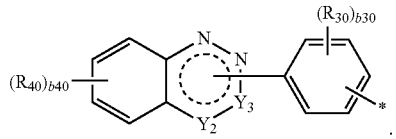

Formula B3-3

In Formulae B3-1 to B3-3, $CY_1$ and $CY_2$ may each independently be selected from a benzene group, a naphthalene group, an anthracene group, a pyrene group, and a phenanthrene group, $R_1$ and $R_2$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, $R_1$ and $R_2$ may optionally be linked to form a —$(Y_1)_{k1}$— linking group, wherein $Y_1$ may be —O—, —S—, or —C(=O), and k1 may be an integer from 1 to 3, one of $Y_2$ and $Y_3$ may be N, and the other may be a single bond, a double bond, or —C(=O), $R_{10}$, $R_{20}$, $R_{30}$, and $R_{40}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, b10 may be an integer from 1 to 7, b20 may be an integer from 1 to 3, b30 and b40 may each independently be an integer from 1 to 4, at least one $R_{10}$, at least one $R_{20}$, and at least one $R_{30}$ may each independently be a hydroxyl group, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$ and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$ and $-P(=O)(Q_{31})(Q_{32})$, $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group, and

* indicates a binding site to a neighboring atom.

In one embodiment, in Formulae B3-1 to B3-3, $R_1$ and $R_2$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, and $R_1$ and $R_2$ may be linked to form a $-(Y_1)_{k1}-$ linking group, wherein $-(Y_1)_{k1}-$ may be —O—, —S— or —C(=O)—.

For example, $R_1$ and $R_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group, and $R_1$ and $R_2$ may be linked to form a $-(Y_1)_{k1}-$ linking group, wherein $-(Y_1)_{k1}-$ may be —O—, —S— or —C(=O)—.

In one embodiment, in Formulae B3-1 to B3-3, $R_{10}$, $R_{20}$, $R_{30}$, and $R_{40}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

For example, $R_{10}$, $R_{20}$, $R_{30}$, and $R_{40}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

In one embodiment, $A_1$ may be a group represented by one selected from Formulae B4-1 to B4-30:

B4-1
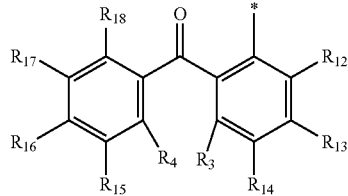

B4-2
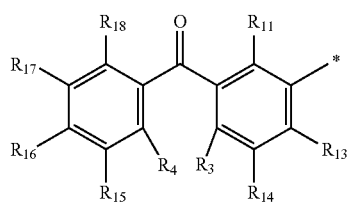

B4-3
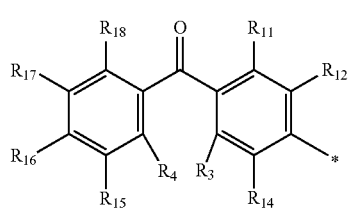

B4-4
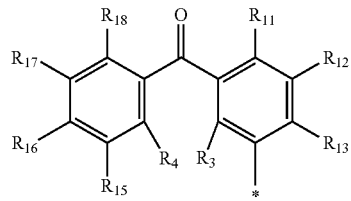

B4-5
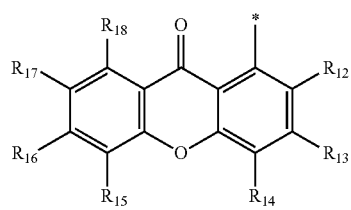

B4-6
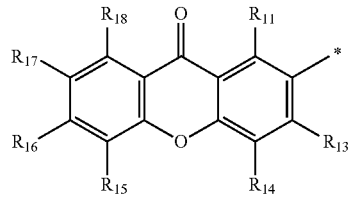

B4-7
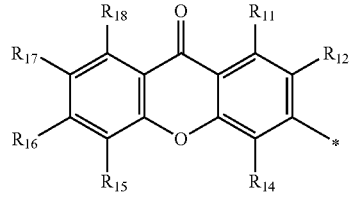

B4-8
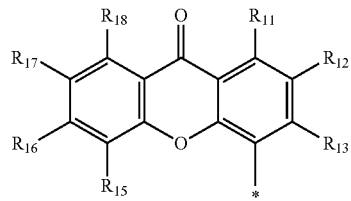

B4-9
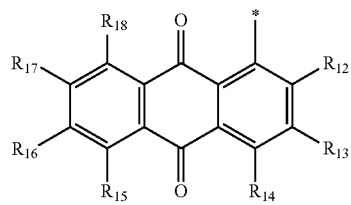

B4-10
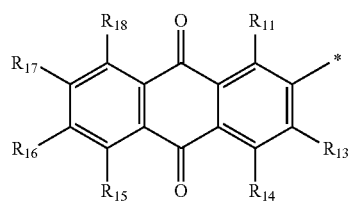

B4-11 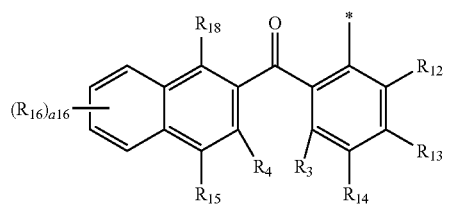
B4-12 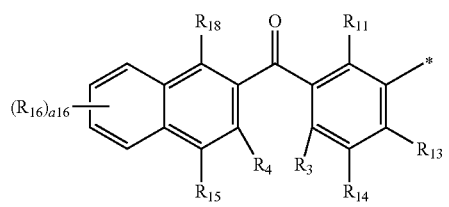
B4-13 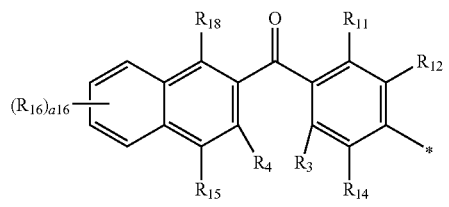
B4-14 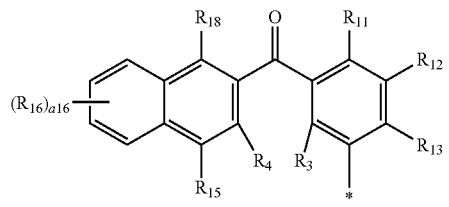
B4-15 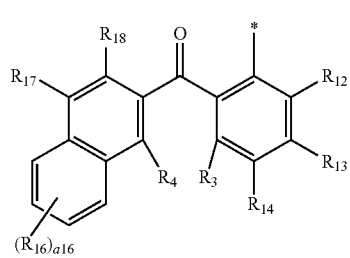
B4-16 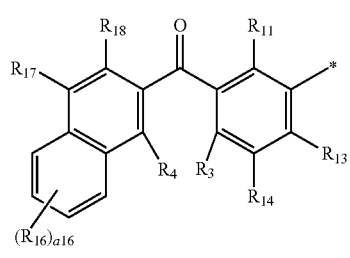
B4-17 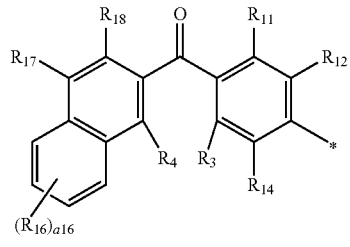
B4-18 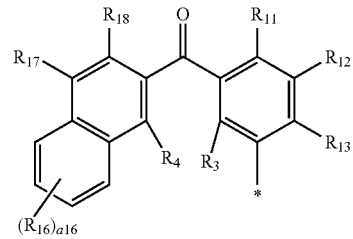
B4-19 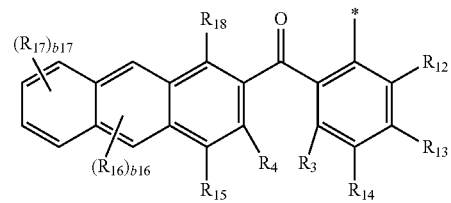
B4-20 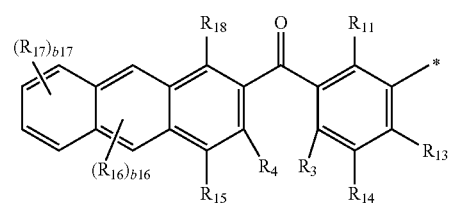
B4-21 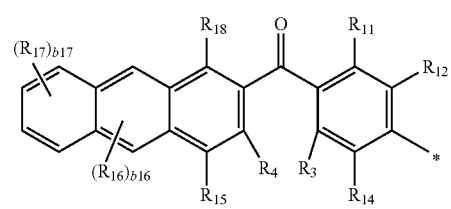
B4-22 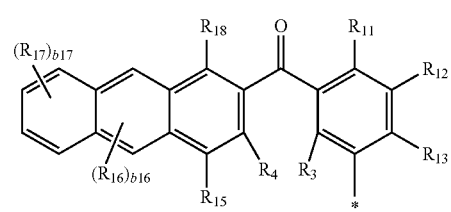
B4-23 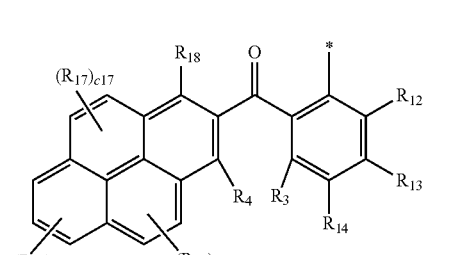
B4-24 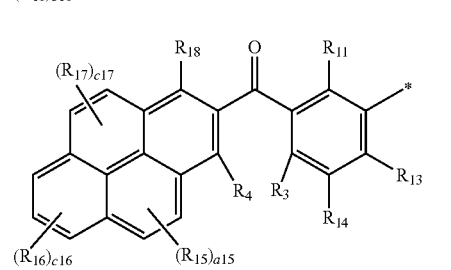

In Formulae B4-1 to B4-30,
$R_3$, $R_4$, and $R_{11}$ to $R_{18}$ are the same as described in connection with $R_{10}$,
a16 may be 1, 2, 3, or 4,
b16 may be 1 or 2,
b17 may be 1, 2, 3, or 4,
c15 may be 1 or 2,
c16 may be 1, 2, or 3,
c17 may be 1 or 2,
$R_{21}$ to $R_{23}$ are the same as described in connection with $R_{20}$,
$R_{31}$ to $R_{35}$ are the same as described in connection with $R_{30}$,
$R_{41}$ to $R_{44}$ are the same as described in connection with $R_{40}$,
at least one of $R_{11}$ to $R_{18}$, at least one of $R_{21}$ to $R_{23}$, and at least one of $R_{31}$ to $R_{35}$ may be a hydroxyl group, and
* indicates a binding site to a neighboring atom.

In one embodiment, at least one $R_{11}$, $R_{15}$, and $R_{18}$ in Formulae B4-1 to B4-26 may be a hydroxyl group. For example, $R_{11}$ may be a hydroxyl group, but embodiments of the present disclosure are not limited thereto.

In one or more embodiments, $R_{21}$ in Formula B4-27 may be a hydroxyl group.

In one or more embodiments, at least one of $R_{31}$ and $R_{35}$ in Formulae B4-28 to B4-30 may be a hydroxyl group. For example, $R_{31}$ may be a hydroxyl group, but embodiments of the present disclosure are not limited thereto.

In one embodiment, $A_1$ may be a group represented by one selected from Formulae B5-1 or B5-2:

In Formulae B5-1 and B5-2,
$R_{14}$, $R_{15}$, and $R_{16}$ are each independently the same as described in connection with $R_{10}$, and
* indicates a binding site to a neighboring atom.

In Formula B1, $A_2$ may be a radical-scavenging group.

In one embodiment, $A_2$ may include at least one compound selected from a phenol-containing compound, a hindered amine-containing compound, and a phenylenediamine-containing compound.

The phenol-containing compound may be BHA, BHT, TBHQ, PG, catecol(1,2-benzenediol), 1,2-naphthalenediol, or the like.

The hindered amine-containing compound may be bis-(2,2,6,6-tetramethyl-4-piperidyl)sebacate, bis-(N-methyl-2,2,6,6-tetramethyl-4-piperidyl)sebacate, bis-(1,2,2,6,6-pentamethyl-4-piperidyl)sebacate, 1,2,2,6,6-pentamethyl-4-piperidyl-tridecyl-1,2,3,4-butanetetracarboxylate, tetrakis-(2,2,6,6-tetramethyl-4-piperidyl)-1,2,3,4-butanetetracarboxylate, tetrakis-(N-methyl-2,2,6,6-tetramethyl-4-piperidyl)-1,2,3,4-butanetetracarboxylate, or the like.

The phenylenediamine-containing compound may be o-phenylenediamine, m-phenylenediamine, p-phenylenediamine, or the like; or o-phenylenediamine, m-phenylenediamine, or p-phenylenediamine, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, and a $C_1$-$C_{20}$ alkoxy group.

In one embodiment, $A_2$ may be a group represented by one selected from Formulae B6-1 to B6-3:

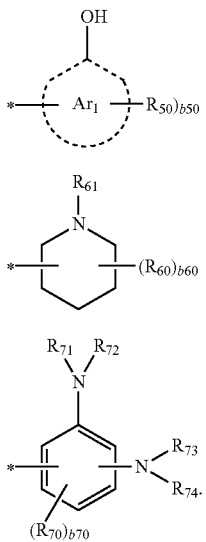

In Formulae B6-1 to B6-3, $Ar_1$ may be a benzene ring or a naphthalene ring, $R_{50}$, $R_{60}$, $R_{61}$, and $R_{70}$ to $R_{74}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, b50 may be an integer from 1 to 6, b60 may be an integer from 1 to 4, b70 may be an integer from 1 to 3, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$ and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group, and

* indicates a binding site to a neighboring atom.

In one embodiment, $R_{50}$, $R_{60}$, $R_{61}$, and $R_{70}$ to $R_{74}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

In one embodiment, $R_{50}$, $R_{60}$, $R_{61}$, and $R_{70}$ to $R_{74}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group.

In one embodiment, $A_2$ may be a group represented by one selected from Formulae B7-1 to B7-3:

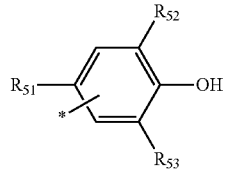

B7-1

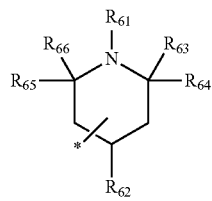

B7-2

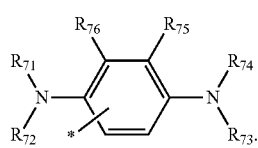

B7-3

In Formulae B7-1 to B7-3, $R_{51}$, $R_{52}$, and $R_{53}$ are each independently the same as described in connection with $R_{50}$, $R_{61}$ to $R_{66}$ are each independently the same as described in connection with $R_{60}$, $R_{71}$ to $R_{74}$ are each independently the same as described in connection with $R_{71}$ to $R_{74}$, $R_{75}$ and $R_{76}$ are each independently the same as described in connection with $R_{70}$, and

* indicates a binding site to a neighboring atom.

In one embodiment, $A_2$ may be a group represented by one selected from Formulae B8-1 to B8-12:

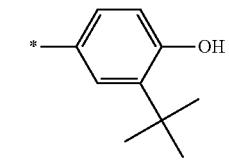

B8-1

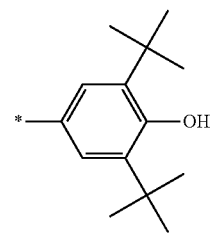

B8-2

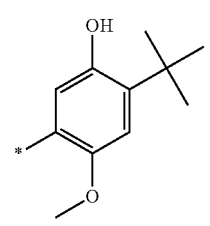

B8-3

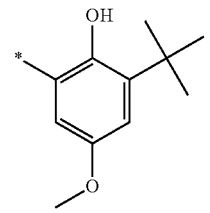

B8-4

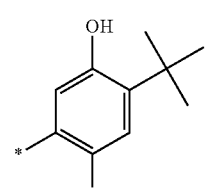

B8-5

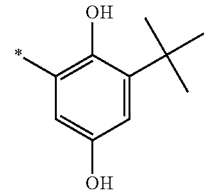

B8-6

-continued

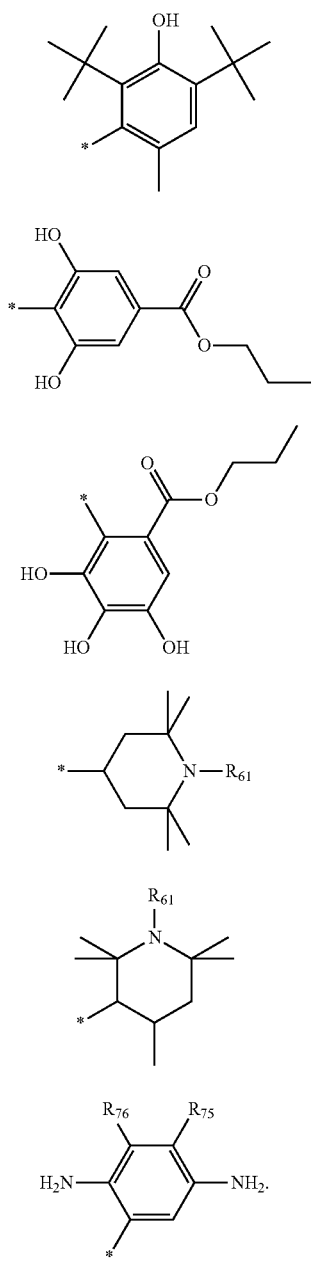

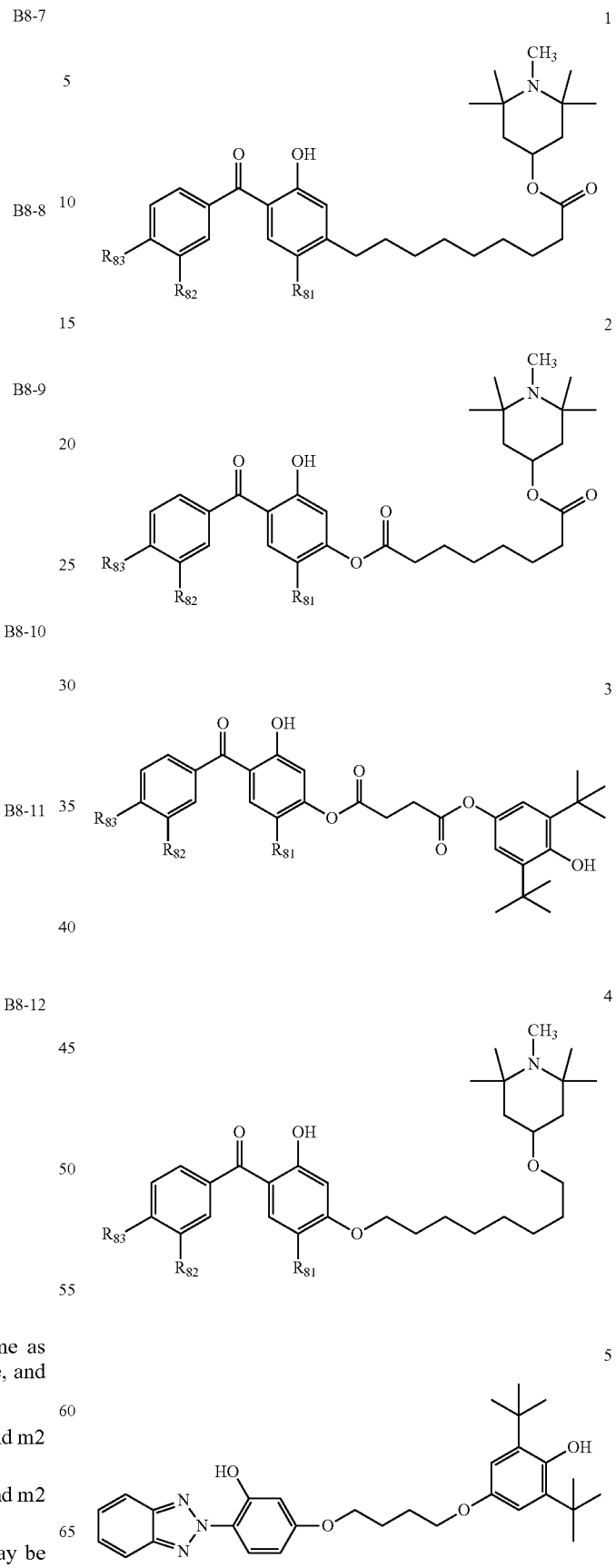

In Formulae B8-1 to B8-12, $R_{61}$, $R_{75}$, and $R_{76}$ are each independently the same as described in connection with $R_{61}$, $R_{75}$, and $R_{76}$ above, and

* indicates a binding site to a neighboring atom.

In Formula B1, m1 may be an integer from 1 to 3, and m2 may be an integer from 1 to 3.

In one embodiment, in Formula B1, m1 may be 1, and m2 may be 1.

In one embodiment, the heterocyclic compound may be selected from Compounds 1 to 14:

6

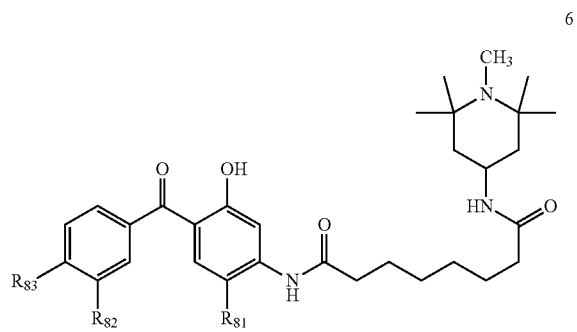

7

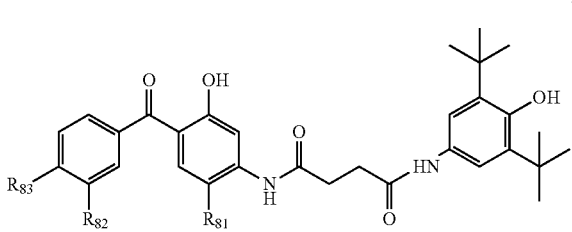

8

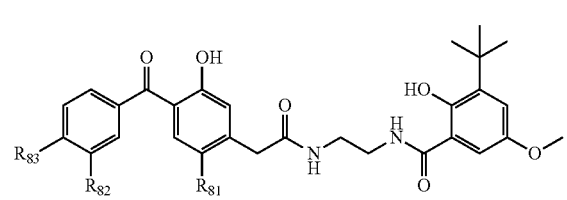

9

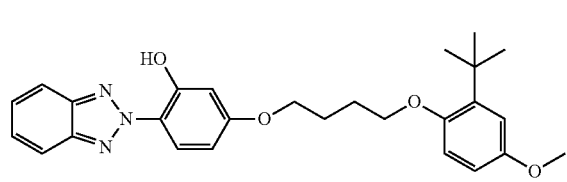

10

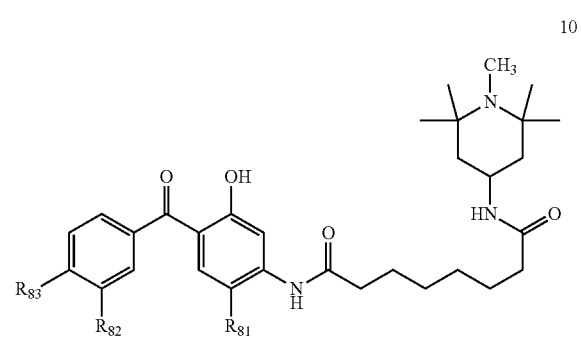

11

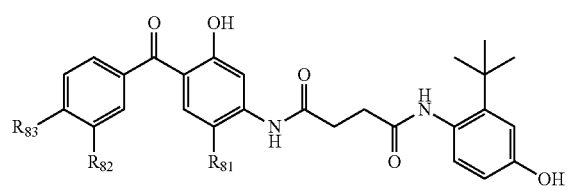

12

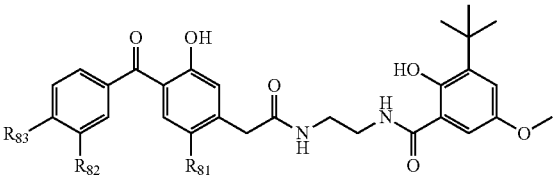

13

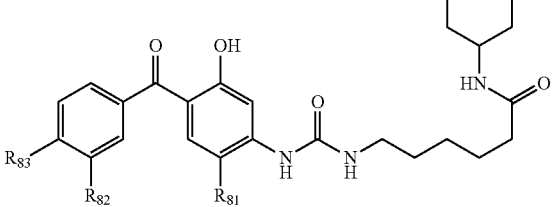

14

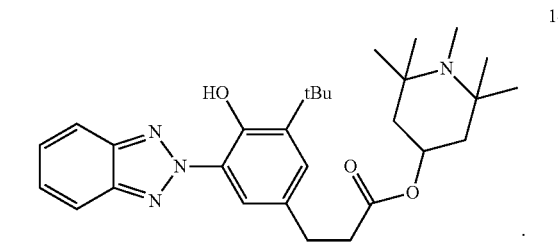

In Compounds 1 to 14, $R_{81}$ to $R_{83}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group.

In one embodiment, the thin film encapsulation composition may include the heterocyclic compound.

The thin film encapsulation composition may include the heterocyclic compound and may further include a solvent.

The solvent may include, for example, di(meth)acrylate, di(meth)acryl-terminated silicon, and diepoxy-terminated silicon, each including at least one selected from a $C_{10}$-$C_{20}$ alkyl group, a $C_{10}$-$C_{20}$ alkoxy group, a $C_{10}$-$C_{20}$ alkenyl group, and a $C_{10}$-$C_{20}$ alkynyl group. In addition, the solvent may further include mono(meth)acrylate and monoepoxy as a diluent.

In one or more embodiment, the solvent may have a visible transmittance of about 70% or more.

The solvent may have a viscosity of about 5 cP to about 10,000 cP.

The thin film encapsulation composition may further include a photoinitiator or a thermal initiator. As the photoinitiator or the thermal initiator, those available in the art may be used without any special limitation.

In one embodiment, the thin film encapsulation composition may include at least two types (or kinds) of the heterocyclic compound.

For example, the thin film encapsulation may include a first heterocyclic compound represented by Formula B1 and a second heterocyclic compound represented by Formula B1, and a wavelength range of light absorbed by the first heterocyclic compound may be different from a wavelength range of light absorbed by the second heterocyclic compound.

In one embodiment, when the thin film encapsulation composition includes at least two types (or kinds) of the heterocyclic compound, the thin film encapsulation formed by using the thin film encapsulation composition may have an average transmittance of about 10% or less in a wavelength range of about 380 nm to about 400 nm, and have an average transmittance of about 60% or more in a wavelength range of about 400 nm to about 430 nm.

In one embodiment, the thin film encapsulation composition may further include a matrix resin monomer, a photopolymerization initiator, and a solvent.

For example, the thin film encapsulation composition may further include a matrix resin monomer. The matrix resin monomer may be a monomer for forming at least one of an acryl-based resin, a methacryl-based resin, an isoprene-based resin, a vinyl-based resin, an epoxy-based resin, a urethane-based resin, a cellulose resin, a perylene-based resin, an imide-based resin, and a silicone-based resin.

In one embodiment, the matrix resin monomer may be a (meth)acryl-based monomer.

In one or more embodiments, the thin film encapsulation composition may further include a photopolymerization initiator. As the photopolymerization initiator, suitable ones available in the art may be used without any special limitation. For example, a photopolymerization initiator that is curable at a wavelength of about 360 nm to about 420 nm may be used.

In one embodiment, the thin film encapsulation composition may further include at least two types (or kinds) of the photopolymerization initiator. For example, one of the at least two types (or kinds) of the photopolymerization initiator may be curable in a UV region (at a wavelength of, for example, about 360 nm to about 420 nm), and the other may be curable in a visible ray region (at a wavelength of, for example, about 400 nm to about 770 nm). In one or more embodiments, the at least two types (or kinds) of the photopolymerization initiator may be all curable in a UV region or a visible ray region.

In one embodiment, the thin film encapsulation composition may further include a matrix resin monomer and a photopolymerization initiator.

The matrix resin monomer may form a matrix resin included in the thin film encapsulation by photopolymerization. For example, the matrix resin monomer may undergo a photopolymerization reaction by the photopolymerization initiator to form the matrix resin included in the thin film encapsulation. The photopolymerization initiator is the same as described above.

In addition, as described above, another aspect of an embodiment provides an electronic apparatus including:
a substrate;
an organic light-emitting device on the substrate; and
a thin film encapsulation sealing the organic light-emitting device,
wherein the thin film encapsulation includes the heterocyclic compound.

The electronic apparatus in which the thin film encapsulation includes the heterocyclic compound may be, for example, an organic light-emitting display apparatus, but embodiments of the present disclosure are not limited to the organic light-emitting display apparatus. The description of the electronic apparatus and the organic light-emitting display apparatus may be understood by referring to the description provided with reference to FIGS. 1-2. In this case, for example, the heterocyclic compound may be used instead of the UV stabilizing mixture.

In one embodiment, the thin film encapsulation 300 may include at least two types (or kinds) of the heterocyclic compound.

For example, the thin film encapsulation may include a first heterocyclic compound represented by Formula B1 and a second heterocyclic compound represented by Formula B1, and a wavelength range of light absorbed by the first heterocyclic compound may be different from a wavelength range of light absorbed by the second heterocyclic compound.

In one embodiment, when the thin film encapsulation includes at least two types (or kinds) of the heterocyclic compound, an average transmittance in a wavelength range of about 380 nm to about 400 nm may be about 10% or less, and an average transmittance in a wavelength range of about 400 nm to about 430 nm may be about 60% or more.

The heterocyclic compound may absorb ultraviolet rays and prevent the ultraviolet rays from penetrating the organic light-emitting device 200 (or reduce a likelihood or amount of the ultraviolet rays that penetrate the organic light-emitting device 200). Therefore, the organic light-emitting display apparatus 10 in which the thin film encapsulation 300 includes the heterocyclic compound may prevent an emission layer, an insulating film or the like, including an organic material, from being damaged by the ultraviolet rays (or may reduce a likelihood or degree of such damage).

In one embodiment, the thin film encapsulation 300 may include at least one organic film, the at least one organic film may include a first organic film, and the first organic film may include the heterocyclic compound.

In one embodiment, the thin film encapsulation (for example, the first organic film) including the heterocyclic compound may have a transmittance of about 10% or less (for example, 8%) with respect to light having a wavelength of about 400 nm to about 410 nm (for example, 405 nm).

In one or more embodiments, the thin film encapsulation (for example, the first organic film) including the heterocyclic compound may have a transmittance of about 80% or more (for example 90%) with respect to light having a wavelength of about 430 nm or more, and may have a transmittance of about 10% or less with respect to light having a wavelength of about 405 nm or less.

In one embodiment, when the first organic film is exposed to light having a maximum emission wavelength of about 405 nm in an exposure amount of about 52,000 $Wh/m^2$, a change in transmittance with respect to a wavelength range of about 400 nm to about 410 nm may be less than about 5%.

In one or more embodiments, when the first organic film is exposed to light having a maximum emission wavelength of about 405 nm in an exposure amount of about 52,000 $Wh/m^2$, a change in transmittance with respect to a wavelength range of about 400 nm to 405 nm may be less than about 3%.

In one or more embodiments, when the first organic film is exposed to light having a maximum emission wavelength in an exposure amount of about 52,000 $Wh/m^2$, a change in transmittance with respect to a wavelength range of about 400 nm to 405 nm may be less than about 1%.

In one or more embodiments, when the first organic film is exposed to light having a wavelength range of about 380 nm to about 410 nm and a maximum emission wavelength of about 405 nm in an exposure amount of about 52,000 $Wh/m^2$, a change in transmittance with respect to a wavelength range of about 400 nm to about 410 nm may be less than about 5%.

In one or more embodiments, when the first organic film is exposed to light having a wavelength range of about 380 nm to about 410 nm and a maximum emission wavelength of about 405 nm in an exposure amount of about 52,000 Wh/m², a change in transmittance with respect to a wavelength range of about 400 nm to about 405 nm may be less than about 3%.

In one or more embodiments, when the first organic film is exposed to light having a wavelength range of about 380 nm to about 410 nm and a maximum wavelength range of about 405 nm in an exposure amount of about 52,000 Wh/m², a change in transmittance with respect to a wavelength range of about 400 nm to about 405 nm may be less than about 1%.

The change in transmittance with respect to the above wavelength range may be measured by, for example, exposing the first organic film by using an LED lamp emitting light having a wavelength range of about 380 nm to about 410 nm and a maximum emission wavelength of about 405 nm.

In one embodiment, a thickness of the first organic film may be in a range of about 10 nm to about 20 μm, for example, about 10 nm to about 10 μm.

In one embodiment, the amount of the heterocyclic compound may be in a range of about 3 parts by weight to about 10 parts by weight based on 100 parts by weight of the first organic film. By controlling the amount of the heterocyclic compound in the first organic film, a maximum absorption wavelength of the first organic film may be finely adjusted, and a UV absorption spectrum may be controlled.

For example, the at least one organic film may consist of the heterocyclic compound.

In one or more embodiments, the at least one organic film may further include, in addition to the heterocyclic compound, a matrix resin, and the heterocyclic compound may be dispersed in the matrix resin. At this time, the heterocyclic compound may be simply dispersed in the matrix resin, or the heterocyclic compound may be cross-linked to the matrix resin.

In one embodiment, the first organic film may further include a matrix resin, and the matrix resin may include at least one of acryl-based resin, a methacryl-based resin, an isoprene-based resin, a vinyl-based resin, an epoxy-based resin, a urethane-based resin, a cellulose resin, a perylene-based resin, an imide-based resin, and a silicone-based resin.

In one or more embodiments, the at least one organic film may further include, in addition to the heterocyclic compound, a photopolymerization initiator. The photopolymerization initiator is the same as described above.

In one or more embodiments, the at least one organic film may further include, in addition to the heterocyclic compound, the matrix resin and the photopolymerization initiator.

Another aspect of an embodiment provides a method of manufacturing an electronic apparatus, the method including:

forming an organic light-emitting device on a substrate; and forming a thin film encapsulation sealing the organic light-emitting device on the substrate, wherein the forming of the thin film encapsulation includes providing a thin film encapsulation composition sealing the organic light-emitting device and curing the thin film encapsulation composition, and the thin film encapsulation composition includes the heterocyclic compound.

The thin film encapsulation, the heterocyclic compound, and the thin film encapsulation composition are the same as described above. When the electronic apparatus is manufactured according to the above-described method, external UV rays are blocked from reaching the organic light-emitting device, thereby preventing a damage from occurring when the organic light-emitting device is continuously exposed to the UV rays (or reducing a likelihood or degree of such damage), and improving the durability of the organic light-emitting device and the electronic apparatus including the same.

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the ring and/or entire group is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire group is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group (e.g., a tetravalent group).

The term "$C_1$-$C_{60}$ heterocyclic group," as used herein, refers to a group having substantially the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, substituted divalent non-aromatic condensed polycyclic group, substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein represents a phenyl group, the term "Me" as used herein represents a methyl group, the term "Et" as used herein represents an ethyl group, the term "ter-Bu" or "Bu$^n$" as used herein, represents a tert-butyl group, and the term "OMe" as used herein represents a methoxy group.

The term "biphenyl group" used herein refers to a "phenyl group substituted with a phenyl group. The "biphenyl group" is a "substituted phenyl group" having a "$C_6$-$C_{60}$ aryl group" as a substituent.

The term "terphenyl group" used herein refers to a "phenyl group substituted with a biphenyl group. The "terphenyl group" is a "phenyl group" having, as a substituent, a "$C_6$-$C_{60}$ aryl group substituted with a $C_6$-$C_{60}$ aryl group."

\* and \*' used herein, unless defined otherwise, each refer to a binding site to a neighboring atom in a corresponding formula.

Hereinafter, a compound according to embodiments and an organic light-emitting device according to embodiments will be described in more detail with reference to Examples. The expression "B was used instead of A" used in describing Synthesis Examples means that an identical number (or substantially identical number) of molar equivalents of A was used in place of molar equivalents of B.

EXAMPLES

Example 1-1

An electronic apparatus including a thin film encapsulation sealing an organic light-emitting device on a substrate was manufactured. The thin film encapsulation was formed by using a thin film encapsulation composition including benzophenone as a UV absorbent and 1,2-naphthalenediol as a radical scavenger.

Comparative Example 1-1

A thin film encapsulation sealing an organic light-emitting device on a substrate was formed by using a thin film encapsulation composition in substantially the same manner as Example 1-1, except that benzophenone was used instead of a UV absorbent and a radical scavenger was not used.

Evaluation Example 1

Figure 3:
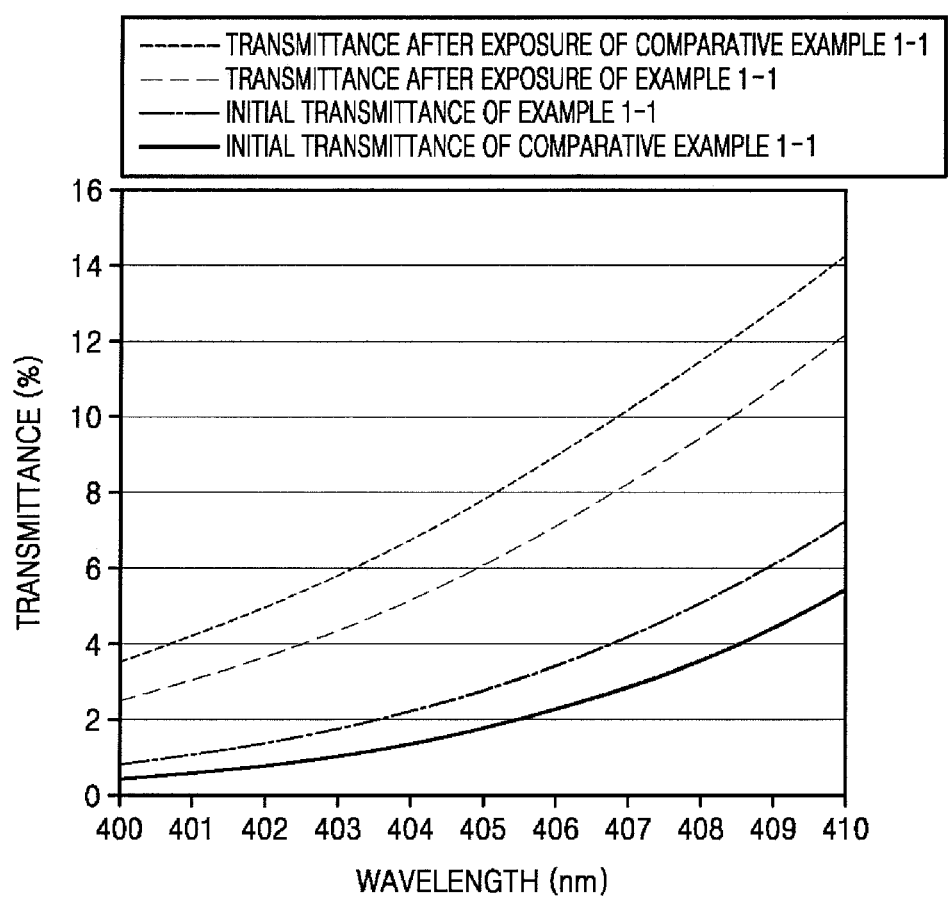
FIG. 3 is a graph showing transmittances of thin film encapsulation portions of an electronic apparatus according to Example 1-1 and an electronic apparatus according to Comparative Example 1-1, with respect to exposure time.

An initial transmittance of the thin film encapsulation of each of the electronic apparatuses manufactured according to Example 1-1 and Comparative Example 1-1 and a transmittance after exposure with an exposure amount of 52,000 Wh/m$^2$ for 30 minutes ("transmittance after exposure") were measured, and results thereof are shown in FIG. 3.

Referring to FIG. 3, in the electronic apparatus according to Example 1-1, the time necessary for the transmittance of the thin film encapsulation to increase is longer, as compared with Comparative Example 1-1, and thus, it is confirmed that photocuring resistance is excellent. For example, regarding a wavelength of 405 nm, since the electronic apparatus of Comparative Example 1-1 has an initial transmittance of about 2% and a transmittance after exposure of about 8%, a change in transmittance (a value obtained by subtracting an initial transmittance from a transmitted amount after exposure) is about 6%, and transmittance is increased four-fold by 30-minute exposure. In contrast, regarding a wavelength of 405 nm, since the electronic apparatus of Example 1-1 has an initial transmittance of about 3% and a transmittance after exposure of about 6%, the change in transmittance is small, as compared with Comparative Example 1-1.

Therefore, an organic light-emitting display apparatus including a UV stabilizing mixture in an encapsulation may prevent an emission layer, an insulating film, or the like, including an organic material, from being damaged by ultraviolet rays (or may reduce a likelihood or degree of such damage).

Synthesis Example 1: Synthesis of Compound 14

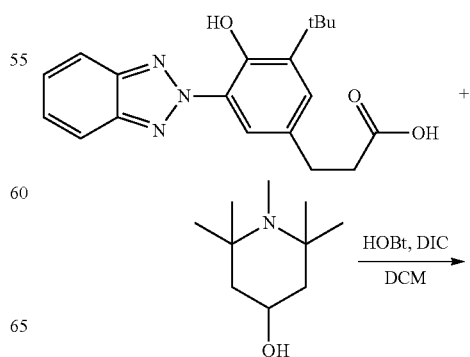

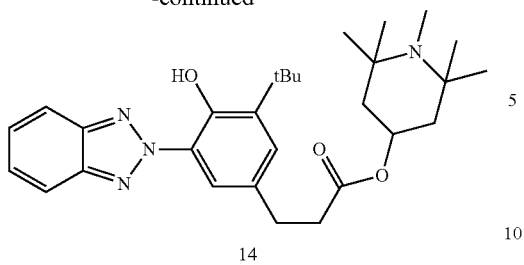

14

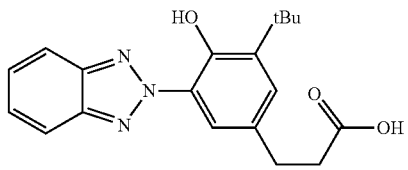

Comparative Example 2-2

A thin film encapsulation sealing an organic light-emitting device on a substrate was formed in substantially the same manner as Example 2-1, except that a mixture in which Compound A and Compound B were mixed at an equivalent of 1:1 was used instead of Compound 14.

As solvents and reagents used for synthesis, commercially available reagents were purchased and used, and those not written were used as purchased. $^1$H-NMR analysis was performed at 25° C. by using a 400 MHz NMR spectrometer, and DMSO-$d_6$ was used as a solvent. Chemical Shift was represented by δ unit (parts per million (ppm)) with reference to $δ_H$ 2.50 of $CHD_2(CD_3)SO$.

3-(3-(2H-Benzo[d][1,2,3]triazol-2-yl)-5-(tert-butyl)-4-hydroxyphenyl)propanoic acid (2 mmol), 4-hydroxy-1,2,2,6,6-pentamethylpiperidine (2.4 mmol), N,N-diisopropylethylamine (4 mmol), 1-hydroxybenzotriazole (HOBt, anhydrous) (2.88 mmol), and diisopropylcarbodiimide (2.88 mmol) were added to 50 mL of dried dimethylchloride solvent and stirred at room temperature. After the reaction was completed, water and ethylacetate were added to the product to extract an organic layer. The organic layer was washed three times by using saturated sodium chloride aqueous solution. Only the extracted organic layer was collected and dried by using magnesium sulfate. Then, the product was purified and separated by flash column chromatography (ethylacetate:n-hexane=9:1), and a solvent was removed through vacuum drying, thereby obtaining a white solid Compound 14 (final yield: 78%).

$^1$H-NMR (400 MHz, DMSO-$d_6$) δ ppm 11.25 (br. S, 1H), 8.00-8.20 (m, 2H), 7.95 (d, J=2.1 Hz, 1H), 7.50-7.67 (m, 2H), 7.28 (d, J=2.1 Hz, 1H), 5.8 (m, 1H), 2.87 (t, J=7.5 Hz, 2H), 2.56 (t, J=7.5 Hz, 2H), 2.35 (s, 3H), 1.80-1.96 (m, 4H), 1.45 (s, 9H), 1.27 (s, 12H).

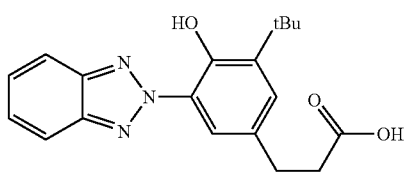

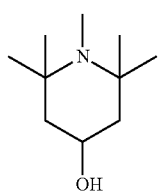

Evaluation Example 2

Example 2-1

An electronic apparatus including a thin film encapsulation sealing an organic light-emitting device on a substrate was manufactured. The thin film encapsulation was formed by using a thin film encapsulation composition including Compound 14 synthesized in Synthesis Example 1.

An initial transmittance ($T_1$) of the thin film encapsulation of each of the electronic apparatuses manufactured according to Example 2-1 and Comparative Examples 2-1 and 2-2 and a transmittance after exposure in an exposure amount of 52,000 Wh/m$^2$ by LED lighting having a maximum emission wavelength of 405 nm ("transmittance after exposure ($T_2$)") were measured, and results thereof are shown in FIG. 3.

In addition, with respect to an initial transmittance ($T_1$) of the thin film encapsulation of each of the electronic apparatuses manufactured according to Example 2-1 and Comparative Examples 2-1 and 2-2 and a transmittance after exposure ($T_2$), a transmittance variation (ΔT %) was calculated as expressed in Equation 1, and is shown in Table 1.

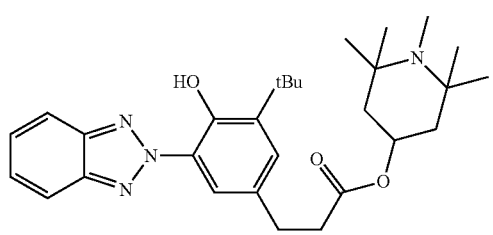

Comparative Example 2-1

A thin film encapsulation sealing an organic light-emitting device on a substrate was formed in substantially the same manner as Example 1, except that Compound A was used instead of Compound 14.

Transmittance Variation(ΔT %)=Transmittance after Exposure($T_2$)−Initial Transmittance($T_1$)     Equation 1

TABLE 1

| | Change in transmittance at 405 nm (ΔT % @405 nm) |
|---|---|
| Example 2-1 | 0.15% |
| Comparative Example 2-1 | 3.50% |
| Comparative Example 2-2 | 4.50% |

Figure 4:
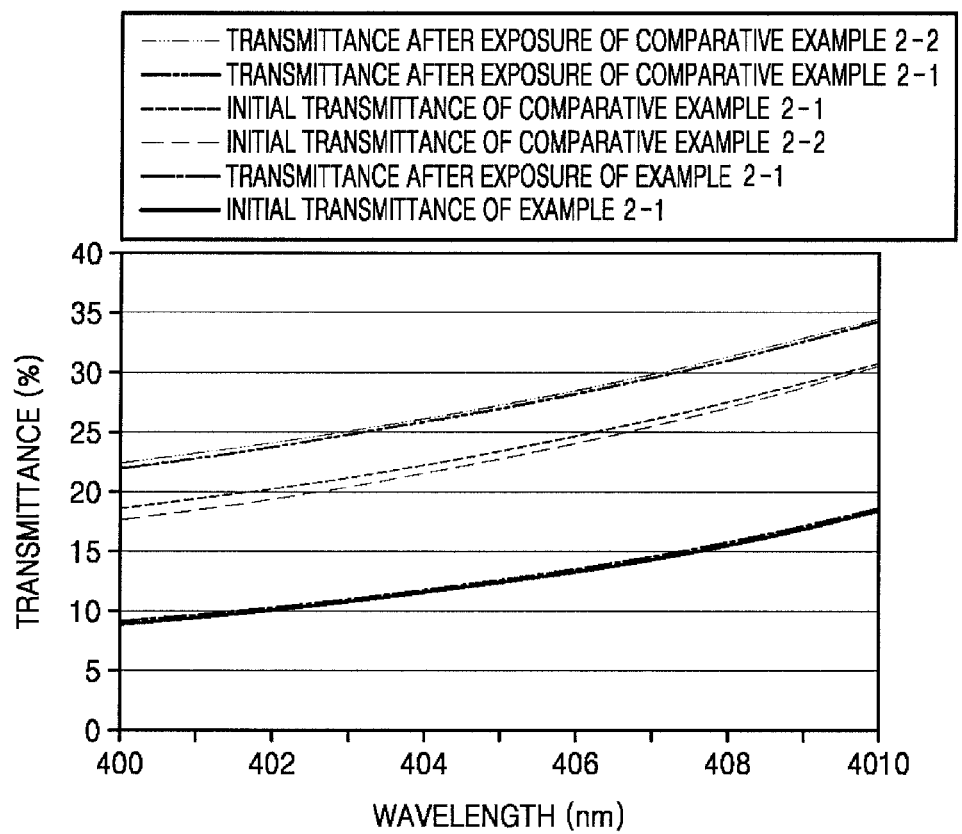
FIG. 4 is a graph showing transmittances of thin film encapsulation portions of the electronic apparatus according to Example 2-1 and electronic apparatuses according to Comparative Examples 2-1 and 2-2, with respect to exposure time.

Referring to FIG. 4 and Table 1, in the electronic apparatus according to Example 2-1, there is almost no change in the initial transmittance and the transmittance after exposure in the thin film encapsulation (change in transmittance: 0.15%), and photocuring resistance is excellent, as compared with the electronic apparatuses according to Comparative Examples 2-1 and 2-2.

Therefore, an organic light-emitting display apparatus including the heterocyclic compound in the encapsulation may prevent an emission layer, an insulating film or the like, including an organic material, from being damaged by ultraviolet rays and visible rays having a short wavelength (or may reduce a likelihood or degree of such damage).

In one or more embodiments, an organic light-emitting display apparatus may prevent an emission layer, an insulating film, or the like, including an organic material, from being damaged by ultraviolet rays (or may reduce a likelihood or degree of such damage).

It should be understood that embodiments described herein should be considered in a descriptive sense only and not for purposes of limitation. Descriptions of features or aspects within each embodiment should typically be considered as available for other similar features or aspects in other embodiments.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An electronic apparatus comprising:
a substrate;
an organic light-emitting device on the substrate; and
a thin film encapsulation portion sealing the organic light-emitting device,
wherein the thin film encapsulation portion comprises an ultraviolet (UV) stabilizing mixture,
the thin film encapsulation portion comprises at least one organic film,
the at least one organic film comprises a first organic film,
the first organic film comprises the UV stabilizing mixture and a matrix resin, and
the UV stabilizing mixture comprises a UV absorbent and a radical scavenger,
wherein (i) the thin film encapsulation portion comprises the first organic film, a second organic film, and a first inorganic film, and the first organic film, the first inorganic film, and the second organic film are sequentially stacked from the organic light-emitting device, or (ii) the thin film encapsulation portion comprises a first inorganic film, a second inorganic film and the first organic film, and the first inorganic film, the first organic film, and the second inorganic film are sequentially stacked from the organic light-emitting device,
wherein the radical scavenger does not include bis-(2,2, 6,6-tetramethyl-4-piperidyl)sebacate,
wherein an amount of the UV stabilizing mixture is in a range of about 3 parts by weight to about 10 parts by weight based on 100 parts by weight of the first organic film, and
the matrix resin consists of at least one selected from a a vinyl-based resin, an epoxy-based resin, a urethane-based resin, a cellulose resin, a perylene-based resin, and an imide-based resin.

2. The electronic apparatus of claim 1, wherein:
the UV absorbent comprises at least one UV-absorbing compound selected from a benzophenone-containing compound, a benzoquinone-containing compound, an anthraquinone-containing compound, a xanthone-containing compound, a benzotriazine-containing compound, a benzotriazinone-containing compound, a benzotriazole-containing compound, a benzoate-containing compound, a cyanoacrylate-containing compound, a triazine-containing compound, an oxanilide-containing compound, a salicylate-containing compound, and a pyrene-containing compound, each substituted with a hydroxyl group.

3. The electronic apparatus of claim 2, wherein:
the UV-absorbing compound is represented by one formula selected from Formulae A1-1 to A1-3:

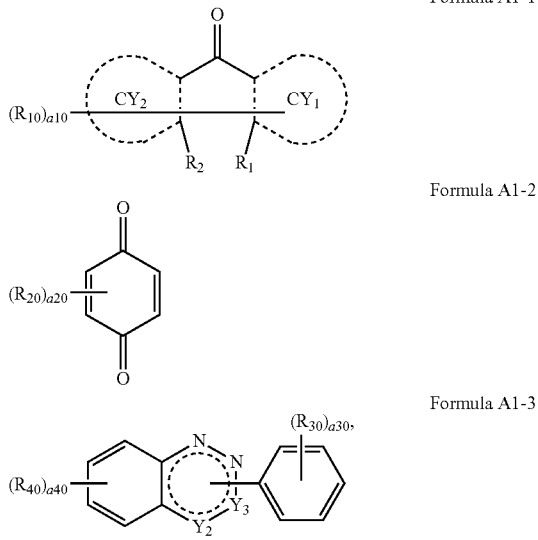

Formula A1-1

Formula A1-2

Formula A1-3 wherein, in Formulae A1-1 to A1-3,
$CY_1$ and $CY_2$ are each independently selected from a benzene group, a naphthalene group, an anthracene group, a pyrene group, and a phenanthrene group,
$R_1$ and $R_2$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
$R_1$ and $R_2$ are optionally linked to form a —$(Y_1)_{k1}$— linking group,
$Y_1$ is —O—, —S—, or —C(=O)—,
k1 is an integer from 1 to 3,
one of $Y_2$ and $Y_3$ is N and the other thereof is a single bond, a double bond, or —C(=O)—,
$R_{10}$, $R_{20}$, $R_{30}$, and $R_{40}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
a10 is an integer from 1 to 18,
a20 is an integer from 1 to 4,
a30 is an integer from 1 to 5,
a40 is an integer from 1 to 4,
at least one of $R_{10}$(s) in the number of a10 is a hydroxyl group,
at least one of $R_{20}$(s) in the number of a20 is a hydroxyl group,
at least one of $R_{30}$(s) in the number of a30 is a hydroxyl group,
at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;
a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

4. The electronic apparatus of claim 3, wherein:
the UV-absorbing compound is represented by one formula selected from Formulae A2-1 to A2-9:

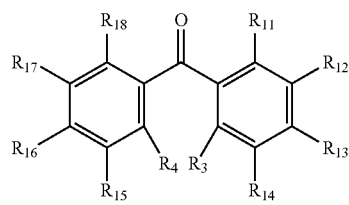
A2-1

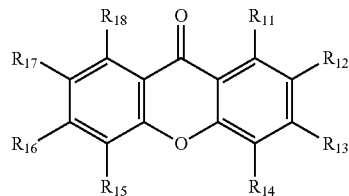
A2-2

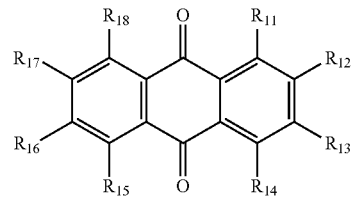
A2-3

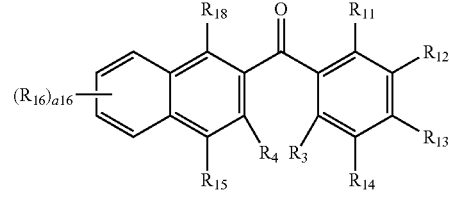
A2-4

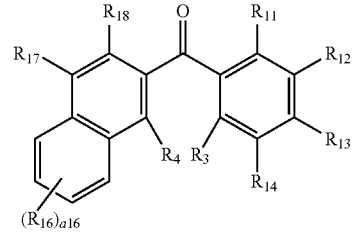
A2-5

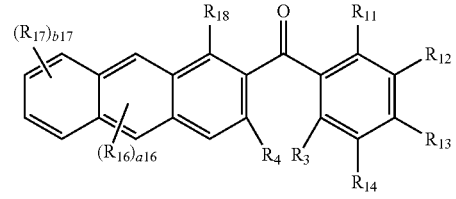
A2-6

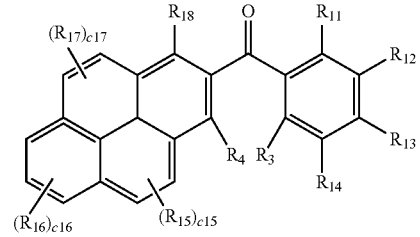
A2-7

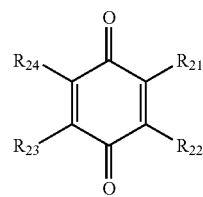
A2-8

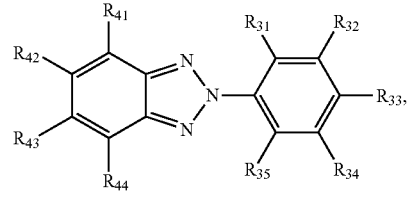
A2-9 wherein, in Formulae A2-1 to A2-9, $R_3$, $R_4$, and $R_{11}$ to $R_{18}$ are the same as described in connection with $R_{10}$ in claim 3, a16 is 1, 2, 3, or 4, b16 is 1 or 2,
b17 is 1, 2, 3, or 4,
c15 is 1 or 2,
c16 is 1, 2, or 3,
c17 is 1 or 2,
$R_{21}$ to $R_{24}$ are the same as described in connection with $R_{20}$ in claim 3,
$R_{31}$ to $R_{35}$ are the same as described in connection with $R_{30}$ in claim 3,
$R_{41}$ to $R_{44}$ are the same as described in connection with $R_{40}$ in claim 3, and
at least one of $R_{11}$ to $R_{18}$, at least one of $R_{21}$ to $R_{24}$, and at least one of $R_{31}$ to $R_{35}$ are each a hydroxyl group.

5. The electronic apparatus of claim 1, wherein:
the UV absorbent absorbs light of a wavelength of about 280 nm to about 430 nm.

6. The electronic apparatus of claim 1, wherein:
the radical scavenger comprises at least one radical-scavenging compound, and
the at least one radical-scavenging compound is selected from a phenol-containing compound, a hindered amine-containing compound, and a phenylenediamine-containing compound.

7. The electronic apparatus of claim 1, wherein:
the radical scavenger comprises at least one compound selected from compounds represented by Formulae A4-1 to A4-3:

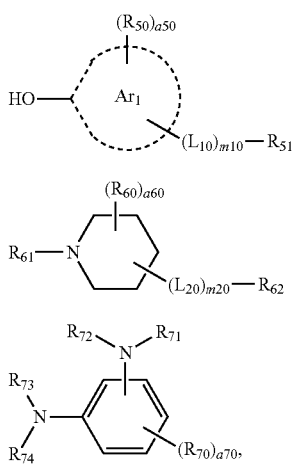

Formula A4-1

Formula A4-2

Formula A4-3 wherein, in Formulae A4-1 to A4-3,
ring $Ar_1$ is a benzene ring or a naphthalene ring,
$L_{10}$ and $L_{20}$ are each independently —O—, —S—, $S(=O)_2$—, —C(=O)—, —C(=O)O—, —C(=O)NH—, a $C_1$-$C_{30}$ hydrocarbon group, a $C_5$-$C_{60}$ carbocyclic group, or a $C_2$-$C_{30}$ heterocyclic group,
m10 and m20 are each independently an integer from 0 to 5,
when m10 is two or more, two or more $L_{10}$(s) are identical to or different from each other, and when m10 is 0, $L_{10}$ is a single bond,
when m20 is two or more, two or more $L_{20}$(s) are identical to or different from each other, and when m20 is 0, $L_{20}$ is a single bond,
$R_{50}$, $R_{51}$, $R_{60}$, $R_{61}$, $R_{62}$, and $R_{70}$ to $R_{74}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
a50 is an integer from 1 to 6,
a60 is an integer from 1 to 4,
a70 is an integer from 1 to 4,
when a50 is two or more, two or more $R_{50}$(s) are identical to or different from each other,
when a60 is two or more, two or more $R_{60}$(s) are identical to or different from each other,
when a70 is two or more, two or more $R_{70}$(s) are identical to or different from each other,
at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;
a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

8. The electronic apparatus of claim 7, wherein:
the radical scavenger comprises at least one compound selected from compounds represented by Formulae A5-1 to A5-4:

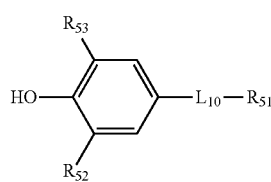

A5-1

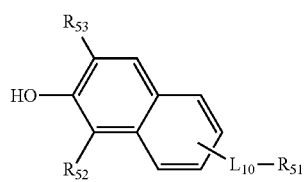

A5-2

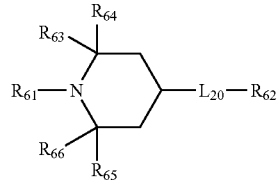

A5-3

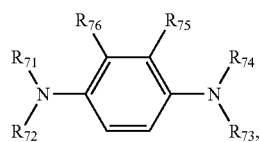

A5-4 wherein, in Formulae A5-1 to A5-4, $R_{51}$ to $R_{53}$, $R_{61}$ to $R_{66}$, and $R_{71}$ to $R_{76}$ are each independently selected from:

deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cyclo alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, and $L_{10}$ and $L_{20}$ are the same as described in claim 7.

9. The electronic apparatus of claim 1, wherein:
an amount of the radical scavenger is in a range of about 0.5 parts by weight to about 20 parts by weight based on 100 parts by weight of the UV absorbent.

10. The electronic apparatus of claim 1, wherein:
the first organic film has a transmittance of about 80% or more with respect to light having a wavelength of about 430 nm or more, and has a transmittance of about 10% or less with respect to light having a wavelength of about 405 nm or less.

11. The electronic apparatus of claim 1, wherein:
when the first organic film is exposed to light in an amount of about 52,000 Wh/m$^2$, a change in transmittance with respect to light having a wavelength of about 400 nm to about 410 nm is less than about 5%.

12. The electronic apparatus of claim 1, wherein:
a thickness of the first organic film is in a range of about 10 nm to about 20 μm.

13. An electronic apparatus comprising:
a substrate;
an organic light-emitting device on the substrate; and
a thin film encapsulation portion sealing the organic light-emitting device, wherein the thin film encapsulation portion comprises an ultraviolet (UV) stabilizing mixture, the thin film encapsulation portion comprises at least one organic film, the at least one organic film comprises a first organic film, the first organic film comprises the UV stabilizing mixture and a matrix resin, and the UV stabilizing mixture comprises a UV absorbent and a radical scavenger, wherein the thin film encapsulation portion comprises a first inorganic film, a second inorganic film and the first organic film, and the first inorganic film, the first organic film, and the second inorganic film are sequentially stacked from the organic light-emitting device, wherein the radical scavenger does not include bis-(2,2,6,6-tetramethyl-4-piperidyl)sebacate, wherein an amount of the UV stabilizing mixture is in a range of about 3 parts by weight to about 10 parts by weight based on 100 parts by weight of the first organic film, and the matrix resin consists of at least one selected from an acryl-based resin, a methacryl-based resin, an isoprene-based resin, a vinyl-based resin, an epoxy-based resin, a urethane-based resin, a cellulose resin, a perylene-based resin, an imide-based resin, and a silicone-based resin.

* * * * *